(12) United States Patent
Carver

(10) Patent No.: US 12,017,035 B2
(45) Date of Patent: Jun. 25, 2024

(54) KEYED INTERLOCKING AIRWAY ASSIST DEVICE

(71) Applicant: Dechoker LLC, Wheat Ridge, CO (US)

(72) Inventor: Alan R. Carver, Erie, CO (US)

(73) Assignee: Dechoker LLC, Wheat Ridge, CO (US)

( * ) Notice: Subject to any disclaimer, the term of this patent is extended or adjusted under 35 U.S.C. 154(b) by 0 days.

(21) Appl. No.: 17/898,670

(22) Filed: Aug. 30, 2022

(65) Prior Publication Data

US 2024/0066280 A1 Feb. 29, 2024

(51) Int. Cl.
*A61M 39/22* (2006.01)
*A61M 39/10* (2006.01)

(52) U.S. Cl.
CPC ............ *A61M 39/22* (2013.01); *A61M 39/10* (2013.01)

(58) Field of Classification Search
CPC .......... A61M 39/10; A61M 2039/1055; A61M 16/0875; A61M 16/20; A61M 16/0463; A61M 16/06; A61M 39/1011; A61M 2039/1027
See application file for complete search history.

(56) References Cited

U.S. PATENT DOCUMENTS

| | | |
|---|---|---|
| 3,809,079 A | 5/1974 | Buttaravoli |
| 3,939,830 A | 2/1976 | da Costa |
| 4,082,095 A | 4/1978 | Mendelson et al. |
| 4,537,189 A | 8/1985 | Vicenzi |
| 4,971,053 A | 11/1990 | Tarrats |
| 5,313,938 A | 5/1994 | Garfield et al. |
| 5,338,166 A | 8/1994 | Schultz |
| 5,611,376 A | 3/1997 | Chuang |
| 5,871,462 A | 2/1999 | Yoder et al. |
| 6,532,956 B2 | 3/2003 | Hil |
| 7,387,062 B2 | 6/2008 | Chen |
| 9,357,905 B2 | 6/2016 | Molnar et al. |
| 10,258,319 B2 | 4/2019 | Arden et al. |
| 10,342,526 B2 | 7/2019 | Arden et al. |
| 10,675,393 B1* | 6/2020 | Carver .................. A61B 17/24 |
| 11,324,877 B2 | 5/2022 | Carver |
| 11,446,460 B1* | 9/2022 | Carver ................ A61M 16/208 |
| 11,633,530 B2 | 4/2023 | He |
| 2001/0035186 A1 | 11/2001 | Hil |
| 2005/0085799 A1 | 4/2005 | Luria et al. |
| 2007/0251528 A1 | 11/2007 | Seitz |
| 2008/0312636 A1 | 12/2008 | Miller et al. |
| 2009/0175747 A1 | 7/2009 | LeBoeuf et al. |
| 2009/0228018 A1 | 9/2009 | Winiarski |

(Continued)

FOREIGN PATENT DOCUMENTS

| | | |
|---|---|---|
| DE | 4208096 A1 | 9/1992 |
| WO | WO 2016/082001 A1 | 6/2016 |

OTHER PUBLICATIONS

PCT International Patent Application No. PCT/US21/36216, International Search Report and Written Opinion of the International Searching Authority dated Oct. 1, 2021, 14 pages.

(Continued)

*Primary Examiner* — Phillip A Gray
(74) *Attorney, Agent, or Firm* — Craig R. Miles; CR MILES P.C.

(57) ABSTRACT

An airway assist device and methods of making and using an airway assist device to assist in opening an airway or removing fluid or material obstructing an airway of a subject.

16 Claims, 15 Drawing Sheets

(56) References Cited

U.S. PATENT DOCUMENTS

| | | | |
|---|---|---|---|
| 2011/0152794 A1 | 6/2011 | Carver | |
| 2012/0221010 A1 | 8/2012 | DeLuca et al. | |
| 2013/0324798 A1 | 12/2013 | Molnar et al. | |
| 2013/0327327 A1 | 12/2013 | Edwards et al. | |
| 2014/0303601 A1* | 10/2014 | Fangrow | A61M 39/10 604/537 |
| 2015/0190158 A1 | 7/2015 | Lih | |
| 2017/0000641 A1 | 1/2017 | Arden et al. | |
| 2017/0266401 A1 | 9/2017 | Arden et al. | |
| 2019/0150962 A1 | 5/2019 | Cutino | |
| 2019/0290873 A1 | 9/2019 | Willett | |
| 2020/0306420 A1 | 10/2020 | Carver | |
| 2022/0008643 A1 | 1/2022 | Carver | |

OTHER PUBLICATIONS

PCT International Patent Application No. PCT/US22/45854, International Search Report and Written Opinion of the International Searching Authority dated Feb. 16, 2023, 13 pages.

Amazon. Dechoker Anti-Choking Device for Adults (Ages 12 Years and up). Website, https://www.amazon.com, review from Oct. 21, 2019, originally downloaded Aug. 10, 2021, 11 pages.

U.S. Appl. No. 12/653,645, filed Dec. 17, 2009.
U.S. Appl. No. 12/928,690, filed Dec. 15, 2010.
U.S. Appl. No. 13/135,783, filed Jul. 15, 2011.
U.S. Appl. No. 13/830,574, filed Mar. 14, 2013.
U.S. Appl. No. 14/794,285, filed Jul. 8, 2015.
U.S. Appl. No. 15/210,944, Office Action dated Feb. 10, 2017.
U.S. Appl. No. 15/210,944, Office Action dated Sep. 20, 2017.
U.S. Appl. No. 15/210,944, Office Action dated Jan. 12, 2018.
U.S. Appl. No. 15/210,944, Office Action dated Jun. 22, 2018.
U.S. Appl. No. 15/210,944, Office Action dated May 20, 2019.
U.S. Appl. No. 15/210,944, Appeal Brief filed Feb. 21, 2019.
U.S. Appl. No. 29/741,865, filed Jul. 16, 2020.
U.S. Appl. No. 16/895,941, Office Action dated Oct. 12, 2021.
U.S. Appl. No. 16/895,941, Office Action dated Dec. 6, 2021.
U.S. Appl. No. 17/484,830, Office Action dated Oct. 29, 2021.
U.S. Appl. No. 17/497,632, Office Action dated Feb. 18, 2022.
U.S. Appl. No. 17/940,143, Office Action dated Dec. 7, 2022.

\* cited by examiner

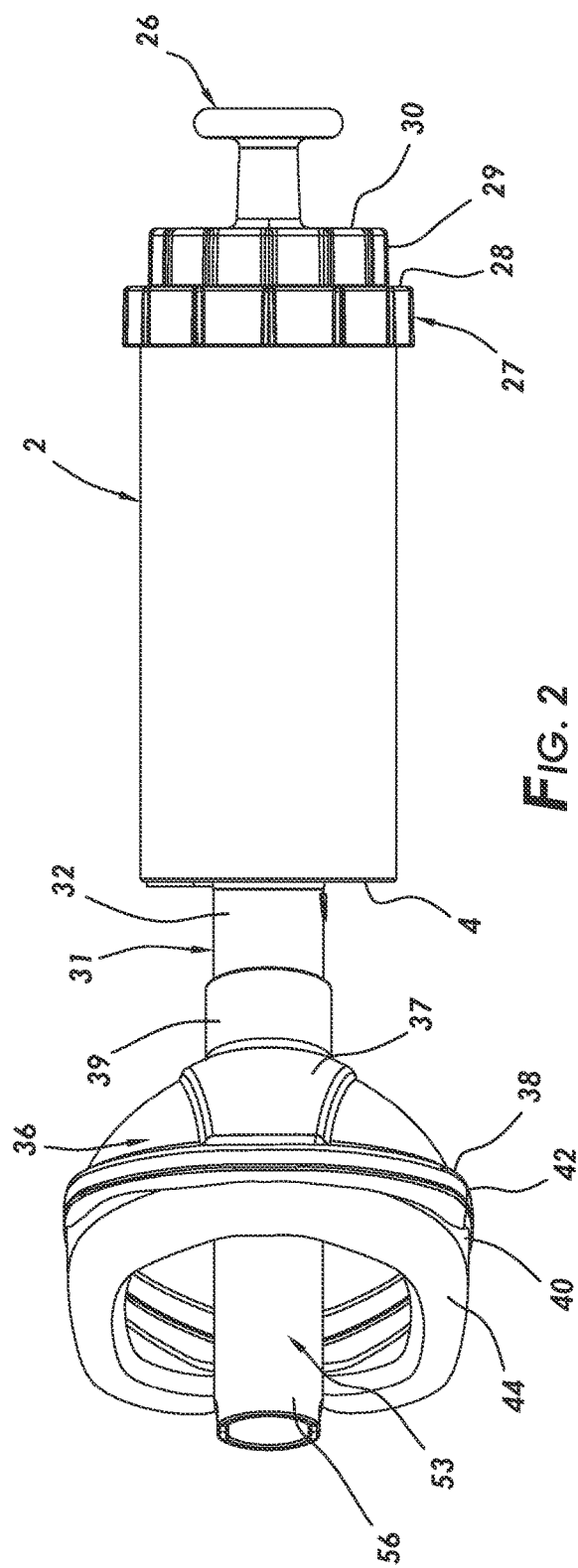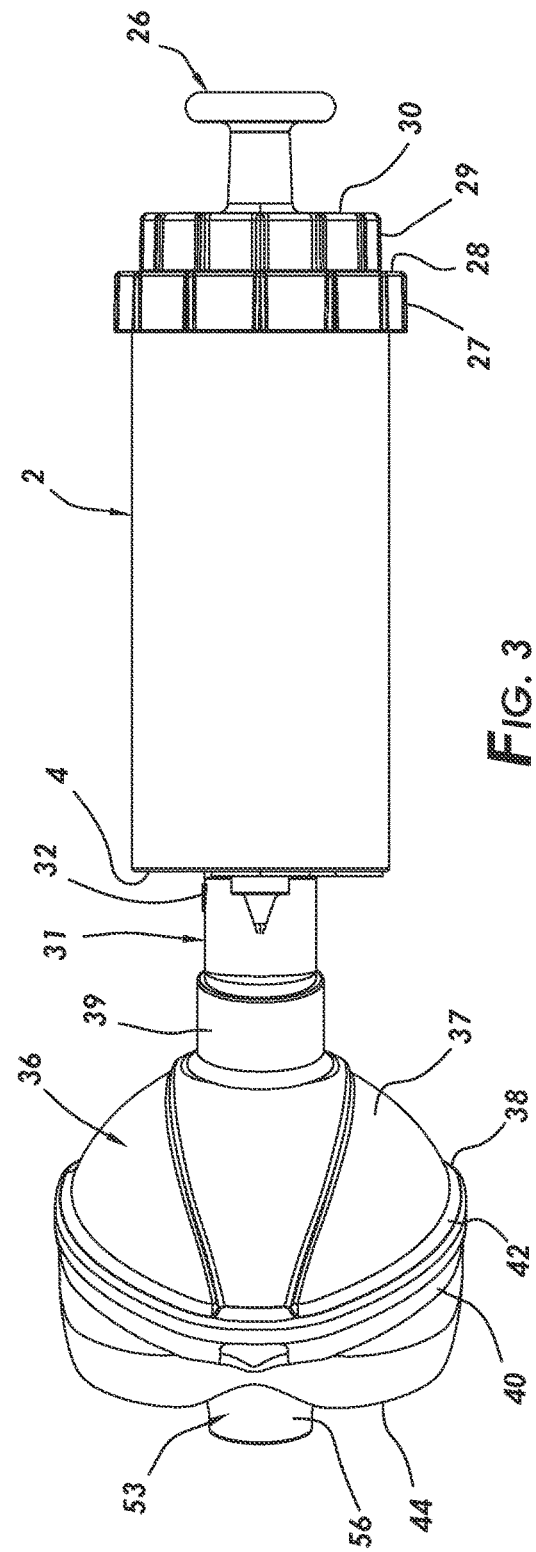

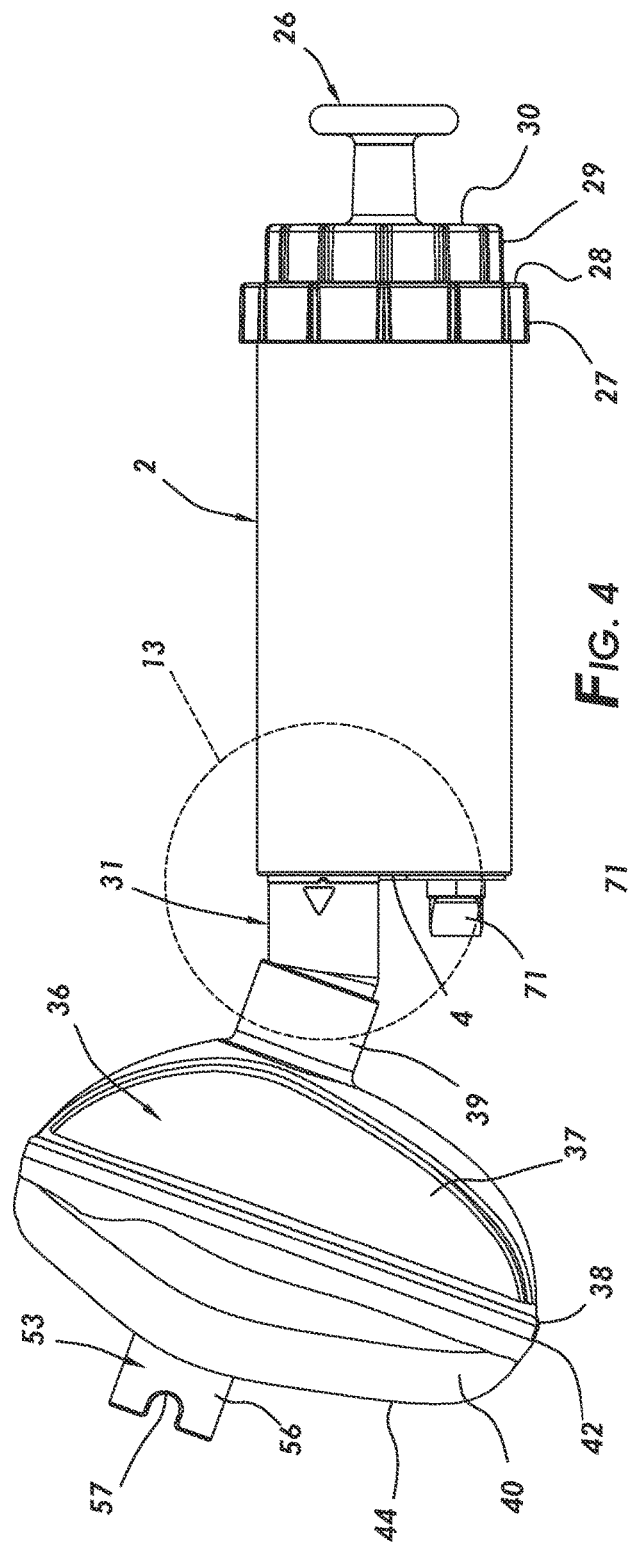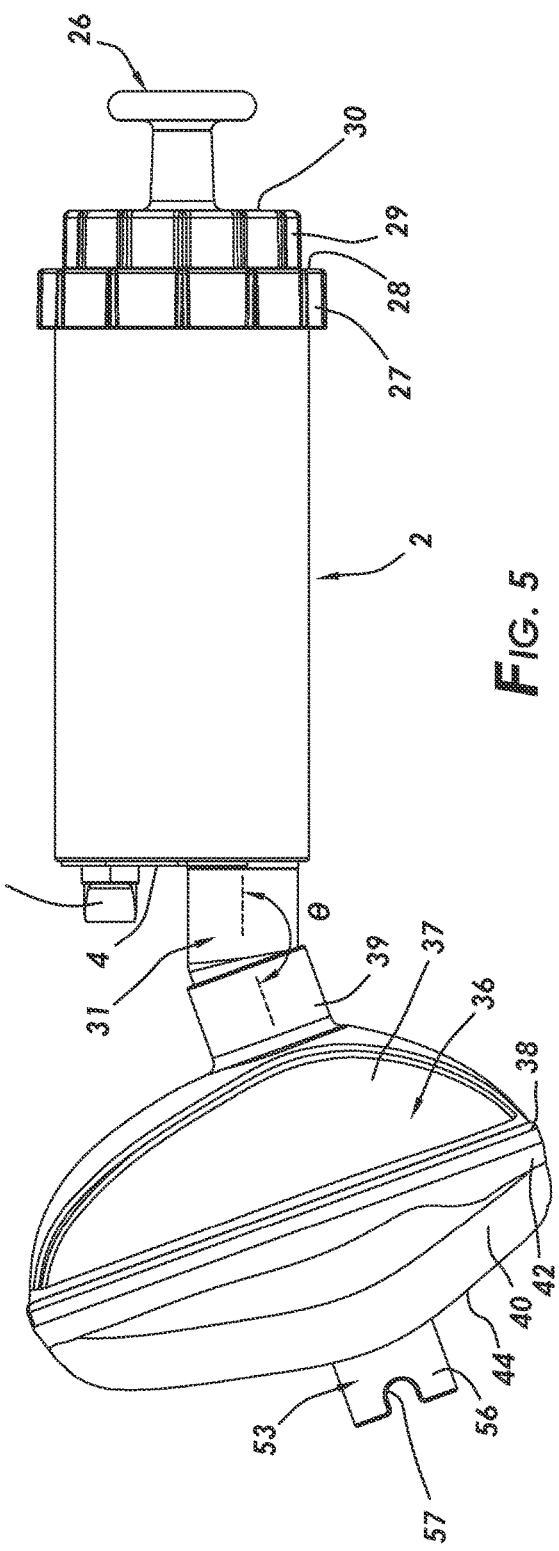

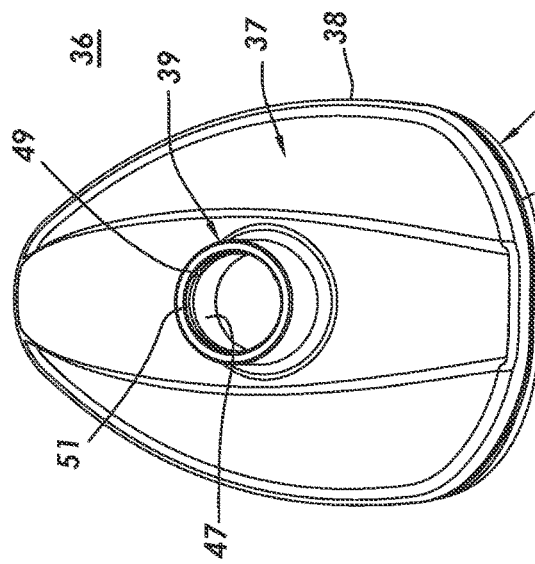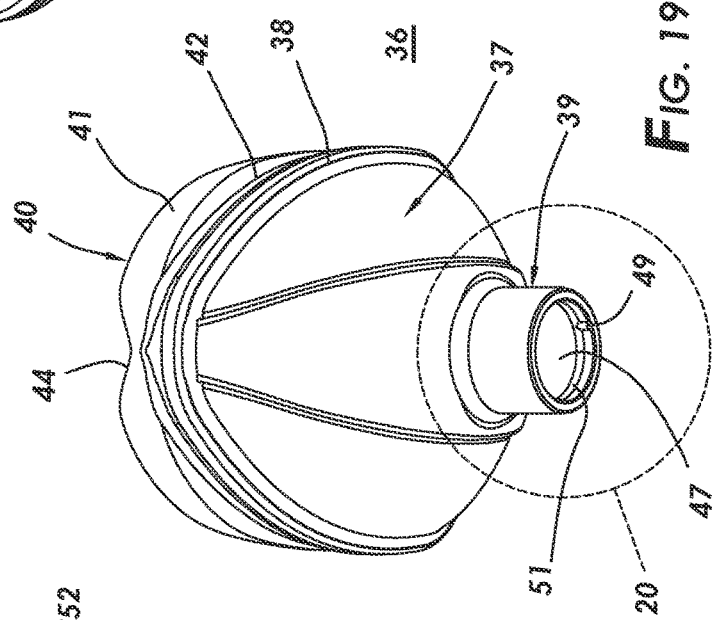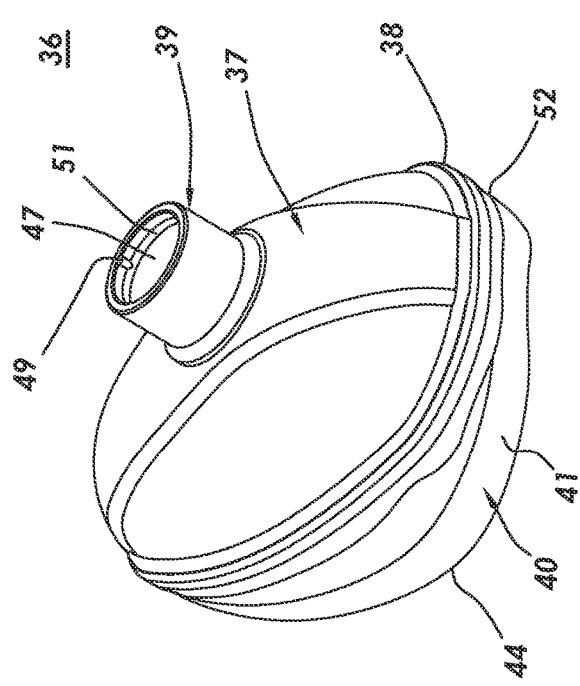

KEYED INTERLOCKING AIRWAY ASSIST DEVICE

I. FIELD OF THE INVENTION

An airway assist device, and methods of making and using an airway assist device, to assist in opening an airway or removing fluid or material obstructing an airway of a subject.

II. BACKGROUND OF THE INVENTION

Conventional airway assist devices have attendant disadvantages that can render the airway assist device inoperable, less effective or difficult to maintenance.

In the first instance, conventional airway assist devices can have component parts that cannot be disassembled which obviates ready replacement of damaged or worn components, interchangeability of components, or disinfection of components.

In the second instance, conventional airway assist devices that include components that can be disassembled can be incorrectly re-assembled in configurations that render the airway assist device inoperable or less effective in opening an airway by removing fluid or material obstructing an airway of a subject.

In the third instance, conventional airway assist devices that include a barrel and a plunger slidably disposed in the barrel may include seals installed to encircle the plunger and engage the internal surface of the barrel to develop suction upon outward draw of the plunger. Over time the seals can become dislodged from, or elongate or twist in relation to, the plunger rendering the airway assist device inoperable or less effective in opening an airway by removing fluid or material obstructing an airway of a subject.

In the fourth instance, conventional airway assist devices that include a barrel and a plunger slidably disposed in the barrel may include valves installed on the barrel to regulate the flow of air into or out of the barrel. Over time the valves can separate from the barrel rendering the airway assist device inoperable or less effective in opening an airway by removing fluid or material obstructing an airway of a subject.

In the fifth instance, conventional airway assist devices may include a face mask having an annular cuff having a solid or inflatable body adapted to seal about the nose and mouth of the subject. The face mask may not be interchangeable between different sizes necessitating purchase of a plurality of airway assist devices to accommodate differences in anatomy between subjects. Additionally, conventional solid or inflatable cuffs, may not seal adequately to allow proper operation of the airway assist device.

Accordingly, there would be substantial advantages in an airway device having components that can be assembled or disassembled and re-assembled in only one correct fixed spatial configuration, and/or having seals or valves bonded to the device to preclude becoming dislodged or misshapen during repeated use, and/or having interchangeable face masks adapted to more effectively seal about the nose and mouth of subject having varying anatomical features.

III. SUMMARY OF THE INVENTION

A broad object of particular embodiments of the invention can be to provide an airway assist device having component parts that can be assembled or disassembled and re-assembled in only one correct fixed spatial relationship useful to assist in opening an airway or removing fluid or material obstructing an airway of a subject.

Another broad object of particular embodiments of the invention can be to provide a face mask having a hollow stem coupled to a dome extending to a dome annular periphery, and a resiliently flexible annular cuff having a body arcuately extending between a cuff first edge and a cuff second edge, wherein the cuff first edge circumferentially couples to the dome annular periphery to dispose the cuff second edge radially inward of the dome annular periphery to present a mask sealing cushion configured to seal about the mouth and nose of a subject.

Another broad object of particular embodiments of the invention can be to provide an airway assist device plunger and/or airway assist device barrel overmolded with a thermoplastic elastomer to form seals and/or valves bonded in fixed spatial relation to the plunger and/or barrel to afford the seals bonded to the plunger as one piece and/or afford the valves bonded to the barrel as one piece.

Naturally, further objects of the invention are disclosed throughout other areas of the specification, drawings, photographs, and claims.

IV. BRIEF DESCRIPTION OF THE DRAWINGS

FIG. 2 is a bottom plan view of the particular embodiment of the airway assist device shown in FIG. 1.

FIG. 3 is top plan view of the particular embodiment of the airway assist device as shown in FIG. 1.

FIG. 4 is first side elevation view of the particular embodiment of the airway assist device as shown in FIG. 1.

FIG. 5 is second side elevation view of the particular embodiment of the airway assist device as shown in FIG. 1.

FIG. 17 is a perspective view of a particular embodiment of a face mask having a hollow stem carrying mateable portions of the first key joint configured to arrest rotation of a face mask in relation to the hollow connector and second keyed joint configured to arrest axial travel of the face mask in relation to the hollow connector.

FIG. 18 is a first end elevation view of a particular embodiment of a face mask depicted in FIG. 17 having a hollow stem carrying mateable portions of the first key joint configured to arrest rotation of a face mask in relation to the hollow connector and second keyed joint configured to arrest axial travel of the face mask in relation to the hollow connector.

FIG. 19 is a first end elevation view of a particular embodiment of a face mask depicted in FIG. 17 having a hollow stem carrying mateable portions of the first key joint configured to arrest rotation of a face mask in relation to the hollow connector and second keyed joint configured to arrest axial travel of the face mask in relation to the hollow connector.

V. DETAILED DESCRIPTION OF THE INVENTION

Figure 1:
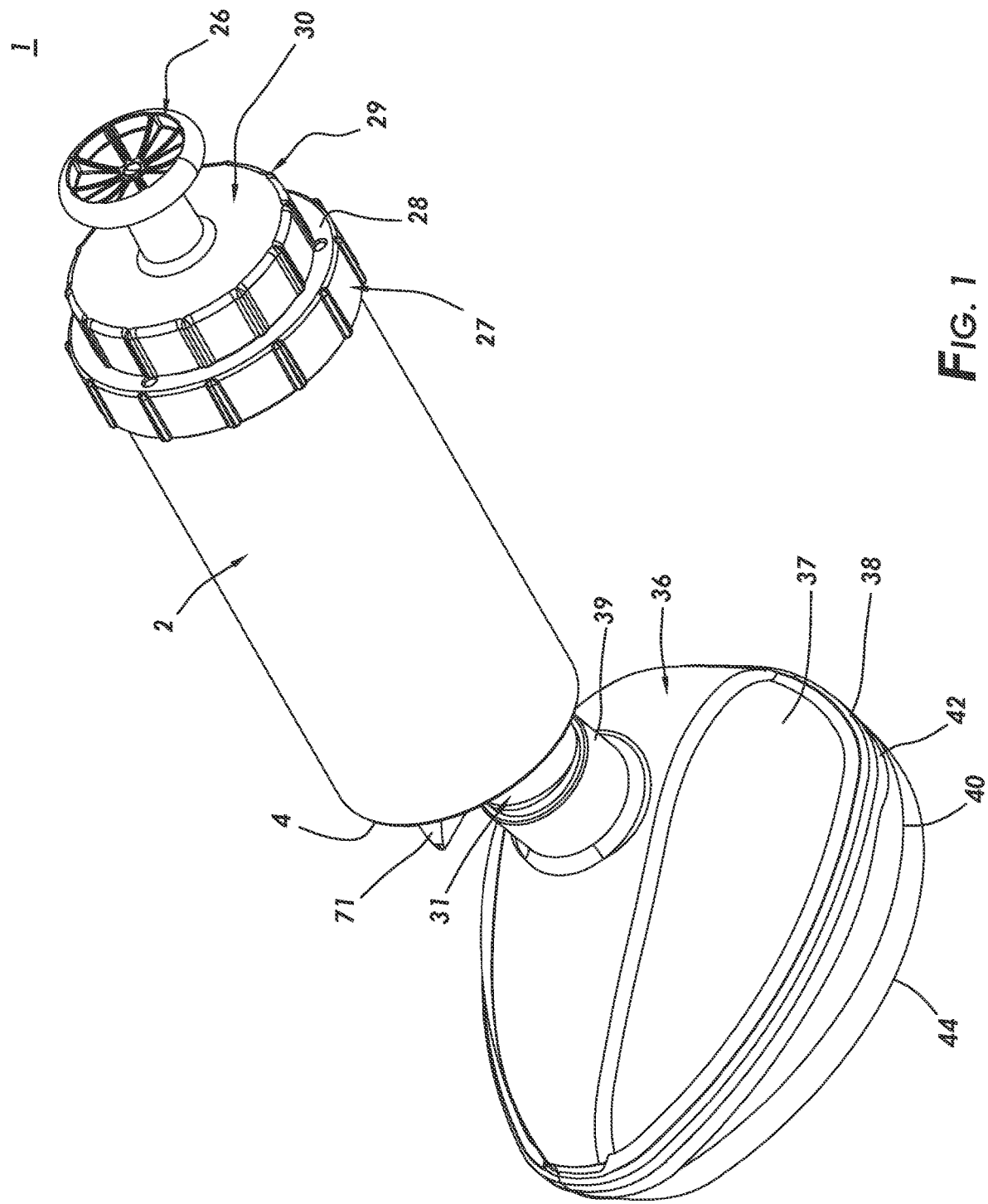
FIG. 1 is a perspective view of a particular embodiment of the airway assist device.
Figure 7:
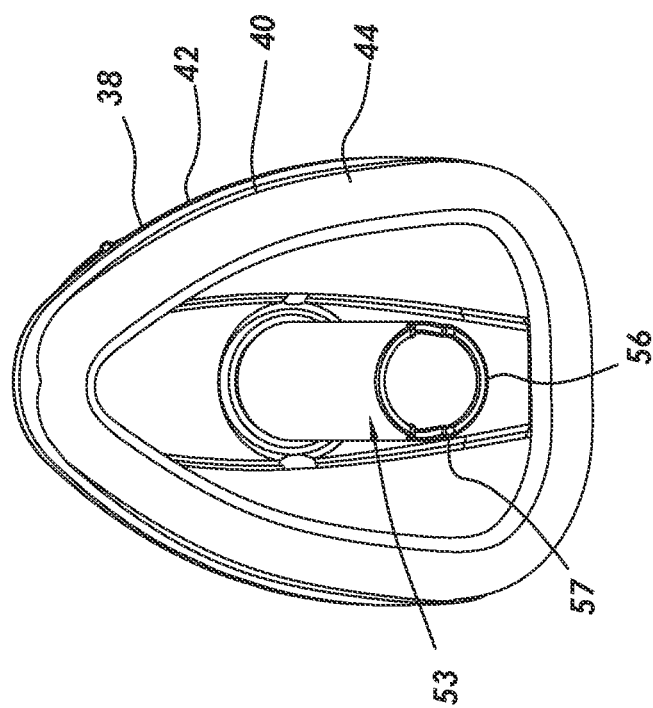
FIG. 7 is second end elevation view of the particular embodiment of the airway assist device as shown in FIG. 1.
Figure 6:
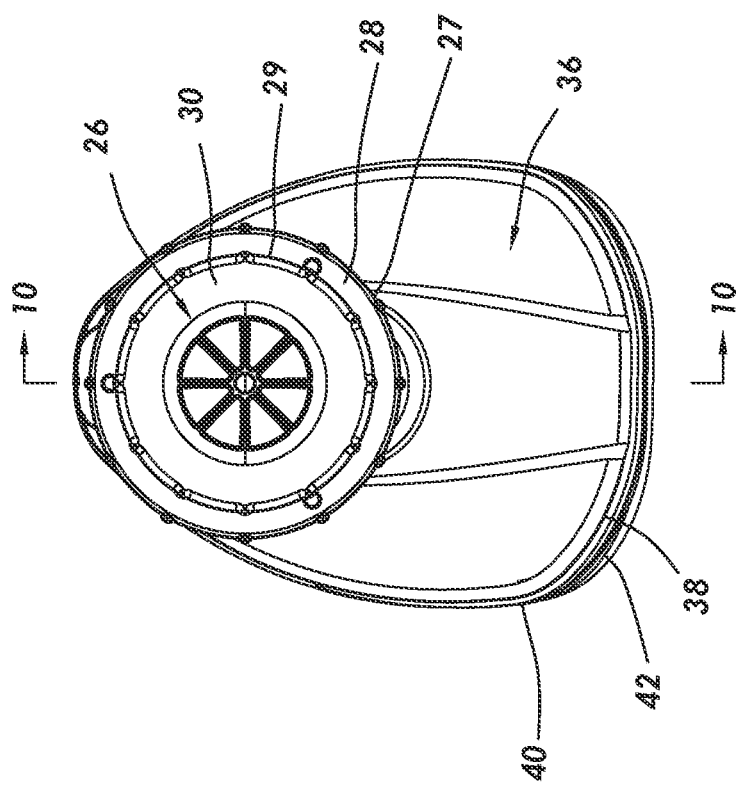
FIG. 6 is first end elevation view of the particular embodiment of the airway assist device as shown in FIG. 1.

Generally, referring to FIGS. 1 through 23, particular embodiments of an airway assist device (1), methods of making an airway assist device (1) and methods of using an airway assist device (1) to assist in opening an airway (A) or removing fluid or material (O) obstructing the airway (A) of a subject (S). In particular embodiments of an airway assist device (1) having interlocking components and making an airway assist device (1) having interlocking components and a method of using an airway assist device (1) including interlocking components.

Now, with primary reference to FIGS. 1 through 13, embodiments of the airway assist device (1) can include a barrel (2) having a barrel proximal end (3) and a barrel distal end (4) joined by a barrel internal surface (5) defining a barrel interior chamber (6). The barrel proximal end (3) can be an open end. The barrel distal end (4) can be a closed end having a barrel extension (7) outwardly extending from said barrel distal end (4). The barrel extension (7) can have a barrel extension internal surface (8) defining a first fluid pathway (9) through a first barrel opening (11) into the barrel interior chamber (6) and a barrel extension external surface (12) carrying a male thread (13). While the Figures depict the barrel (2) as being cylindrical in configuration, this is not intended to preclude other embodiments having different cross-sectional tubular structures including as illustrative examples: an oval, a triangle, a square, a rectangle, a parallelogram, a rhombus, a trapezium, a kite, a polygon including but not necessarily limited to: a pentagon, a hexagon, an octagon, a nonagon, a decagon, and combinations thereof.

Again, with primary reference to FIGS. 1 through 13, a plunger (14) can be slidably disposed within the barrel (2). In particular embodiments, the plunger (14) can include a plunger proximal end (15) opposite a plunger distal end (16) joined by a plunger sidewall (17). The plunger (14) can be configured to reciprocally move within the barrel interior chamber (6). In particular embodiments, the plunger sidewall (17) can be configured to provide an annular space (18) between the plunger sidewall (17) and the barrel internal surface (5) to allow the plunger (14) to move freely in the barrel interior chamber (6). One or more seals (19) can encircle the plunger sidewall (17) bridging the annular space (18) to engage the barrel internal surface (5). In particular embodiments, the one or more seals (19) can be correspondingly disposed in one or more channels (20) encircling the plunger (14). The one or more seals (19) disposed in the one more channels (20) encircling the plunger (14) can outwardly extend from the plunger sidewall (17) bridging the annular space (18) to slidably engage the barrel internal surface (5).

In particular embodiments, two or more concentric rings (21) encircling the plunger sidewall (17) can be disposed in fixed spatial relation a distance apart to form the one or more channels (20) between each pair of concentric rings (21). In particular embodiments the two or more concentric rings (21) can slidably engage the barrel internal surface (5). In other embodiments, the two or more concentric rings (21) can be configured to maintain the annular space (18) between the two or more concentric rings (21) and the barrel internal surface (5) to allow the plunger (14) to move freely in the barrel interior chamber (6). A seal (19) can be disposed in each of the one or more channels (20) to encircle the plunger sidewall (17). The seal(s) (19) disposed in the one or more channels (20) can outwardly extend from the plunger sidewall (17) bridging the annular space (18) to slidably engage the barrel internal surface (5).

Figure 10:
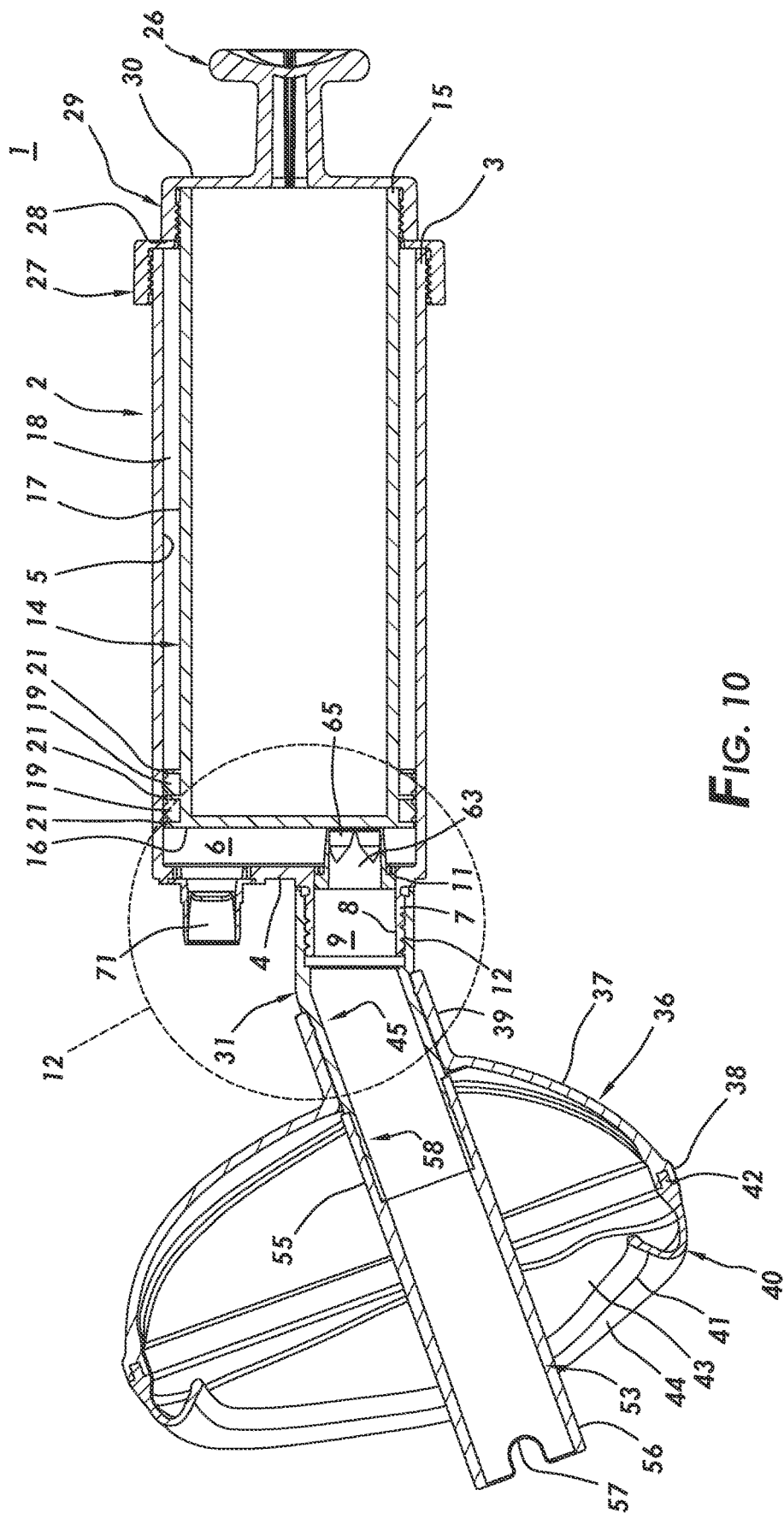
FIG. 10 is a cross section 10-10 of the particular embodiment of the airway assist device as shown in FIG. 5.
Figure 11:
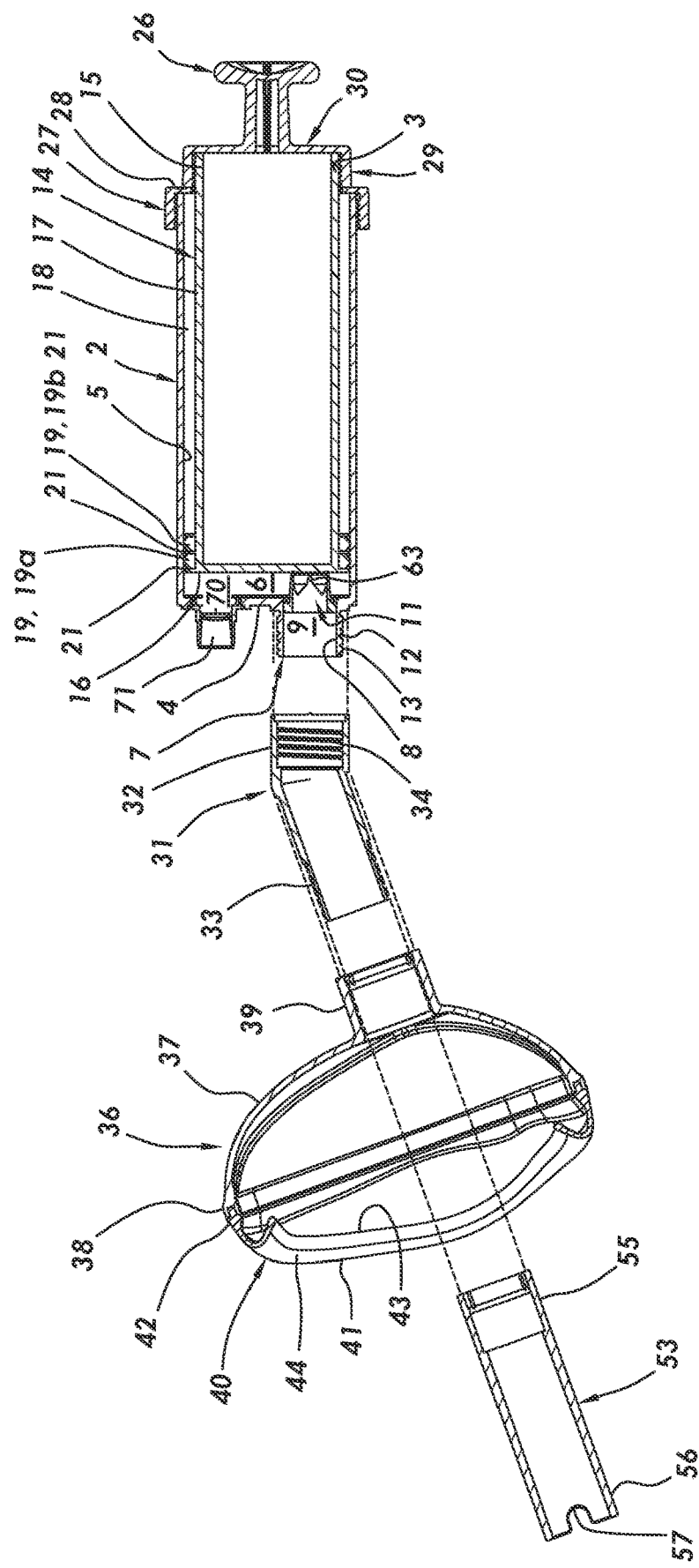
FIG. 11 is an exploded cross section 11-11 depicting the keyed interlocking components of the particular embodiment of the airway assist device as shown in FIG. 5.
Figure 12:
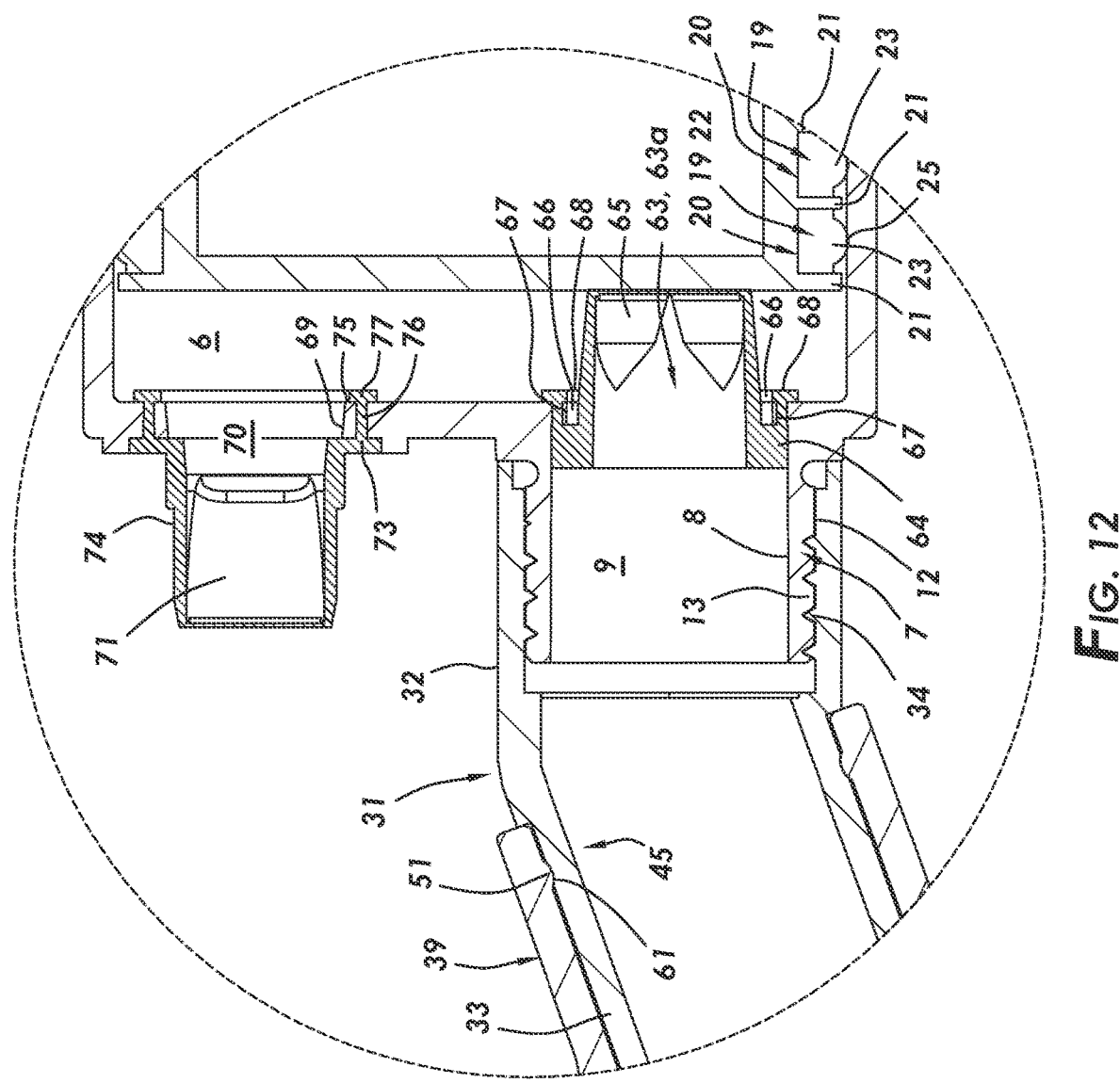
FIG. 12 is an enlarged view 12 depicting certain keyed interlocking and overmolded components of the particular embodiment of the airway assist device as shown in FIG. 10.
Figure 13:
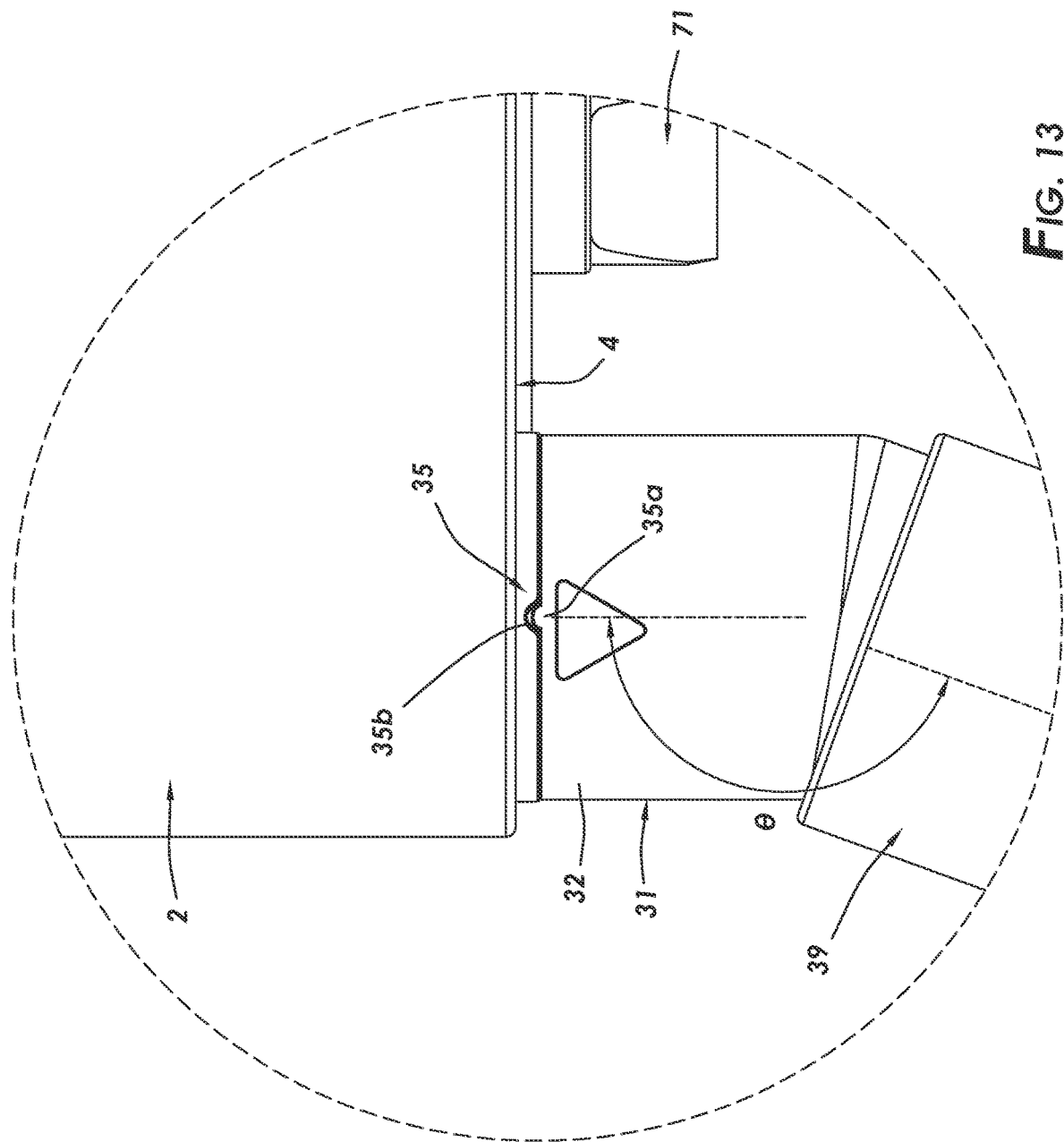
FIG. 13 is an enlarged view 13 depicting certain keyed interlocking components of the particular embodiment of the airway assist device as shown in FIG. 4.

As shown the illustrative examples of FIGS. 10 through 12, three concentric rings (21) can be disposed in spatially fixed spaced apart relation on the plunger sidewall (17) to form a first channel (20a) and a second channel (20b). The three concentric rings (21) can have a configuration to maintain the annular space (18) between the three concentric rings (21) and the barrel internal surface (5) to allow the plunger (14) to move freely in the barrel interior chamber (6). A first seal (19a) can be disposed in first channel (20a) encircling the plunger sidewall (17) and a second seal (19b) can be disposed in the second channel (20b) to encircle the plunger sidewall (17). The seals (19a, 19b) can outwardly extend beyond the three concentric rings (21) bridging the annular space (18) to slidably engage the barrel internal surface (5) of the barrel (2). In particular embodiments, the one or more seals (19) can, but need not necessarily, comprise an O-ring. An O-ring, for the purposes of this invention, comprises a mechanical gasket, typically, but not necessarily, in the shape of a torus including a loop of elastomer with a round cross-section, configured to be seated in a channel (20) and encircling the plunger sidewall (17). The cross-section of the loop of material, while typically round, can take any configuration in cross-section that when seated in the channel (20) can slidably engage the barrel internal surface (5). The O-ring can be compressed between the plunger sidewall (17) and the barrel internal surface (5). As illustrative examples, the seal (19) can have a cross-section that may be square or rectangular or comprise an encircling band with an extending structure that contacts the barrel internal surface (5).

Now, with primary reference to FIG. 12, in particular embodiments, the one or more seals (19) disposed in the corresponding one or more channels (20) can be formed by overmolding the plunger (14) with a thermoplastic elastomer to produce a seamless combination of the one or more seals (19) disposed in the corresponding one or more channels (20) as one piece. In the overmolding process, the barrel (2) can be inserted into an injection mold and molten thermoplastic elastomer can injected to fill the shape of the mold surrounding the channels (20) in the barrel (14).

There can be substantial advantages in overmolding the barrel (14) with a thermoplastic elastomer to produce the seals (19). In the first instance, the thermoplastic elastomer forms a bond with the plastic of the barrel (2) that is maintained during use of the airway assist device (1) in the end-use environment. The bond obviates the long felt but unresolved need to eliminate circumferential elongation (stretch) of the seal (19) or torsion (twist) of the seal (18) in the channel (20) each of which, or the combination thereof, can restrict proper movement of the plunger (14) in the barrel (2). In the second instance, the one or more seals can be formed in a configuration that cannot be achieve using conventional O-rings. In this regard, the overmolded seal (19) can include a seal base (22) which substantially fills and affixes to the channel (20) between a pair of concentric rings (20) and a seal crown (23) extending from the base outward of the pair of concentric rings (20). The plunger (14) slidingly disposed in the barrel (2) engages the seal crown (23) with an internal surface of the barrel (5). The seal crown (23) can be configured to achieve a compression contact area with the barrel internal surface (5) of the barrel (2) that concurrently affords a substantially leak-free seal and permits ready reciprocal movement of the plunger (14) within barrel (2) during normal use. Again, with primary reference to the example of FIG. 12, the seal crown (23) can have a dimension in cross section lesser than the distance between the pair of concentric rings (20), or can be medially disposed on the seal base (22) to define an seal annular space (24) between the seal crown (23) and each of the pair of concentric rings (20), or can have an arcuate compression surface (25), or a combination thereof, to afford a substantially leak-free seal and reduced resistance to reciprocal movement within the barrel (2).

Again, with primary reference to FIGS. 1 through 11, in particular embodiments, a handle (26) can be connected to the plunger (14) and extending outward of the barrel proximal end (3). The handle (26) can be configured in any manner that extends outward of the barrel proximal end (3) and can receive pulling forces (PF1) or pushing forces (PF2) to correspondingly reciprocally move the plunger (14) inside the barrel (2) between the barrel distal end (4) and the barrel proximal end (3). In the illustrative example shown in the Figures, the plunger (14) can comprise a tubular member having a plunger length (PL) disposed between the plunger distal end (16) opposite the plunger proximal end (16) extending outwardly of the barrel proximal end (3). A handle (26) can be attached to plunger proximal end (15). The handle (26) can be configured to be readily grasped by a hand to apply pulling forces (PF1) or pushing forces (PF2) to correspondingly reciprocally move the plunger (14) in the barrel (2). However, the illustrative example of the Figures is not intended to preclude embodiments in which the handle (26) comprises an elongate member connected directly to the plunger (14) and extending outward of the barrel proximal end (3). As an illustrative example, the elongate member can be a thin straight rod.

Again, with primary reference to FIGS. 1 through 11, in particular embodiments, a retainer ring (27) having a radially inwardly extending retainer ring shoulder (28) can be coupled to the barrel proximal end (3). The retainer ring shoulder (28) can radially inwardly extend a distance sufficient to prevent removal of the plunger (14) from the barrel (2). In particular embodiments, the plunger (14) can engage the retainer ring shoulder (28) when drawn toward the barrel proximal end (3). In the illustrative embodiments shown in the Figures, one of the concentric rings (20) disposed on and encircling the plunger (14) can engage the retainer ring shoulder (28) when drawn toward the open barrel proximal end (3) to prevent removal of the plunger (14) from the barrel (2).

In particular embodiments, a portion of the plunger (14) or the handle (26) can be configured to radially outwardly extend to engage the retaining ring shoulder (28) when the plunger (14) is pushed toward the barrel distal end (4) to prevent the plunger (14) from engaging the barrel distal end (4). In the embodiments shown in the Figures, the plunger proximal end (15) extending outward of the barrel proximal end (3) can have a plunger proximal end annular member (29) that outwardly radially extends a sufficient distance to engage the retainer ring shoulder (28) when the plunger (14) moves toward the barrel distal end (4) to prevent the plunger from engaging the barrel distal end (4). In particular embodiments, the retainer ring (27) and the plunger proximal end annular member (29) can correspondingly threadingly couple the open barrel proximal end (3) and the plunger proximal end (15) which allows for removal of the retainer ring (27) or the plunger proximal end annular member (29) to allow removal of the plunger (14) from the barrel (2). In particular embodiments, the plunger proximal end annular member (29) can be a part of a plunger cap (30) coupled to the plunger proximal end (15).

Figure 16:
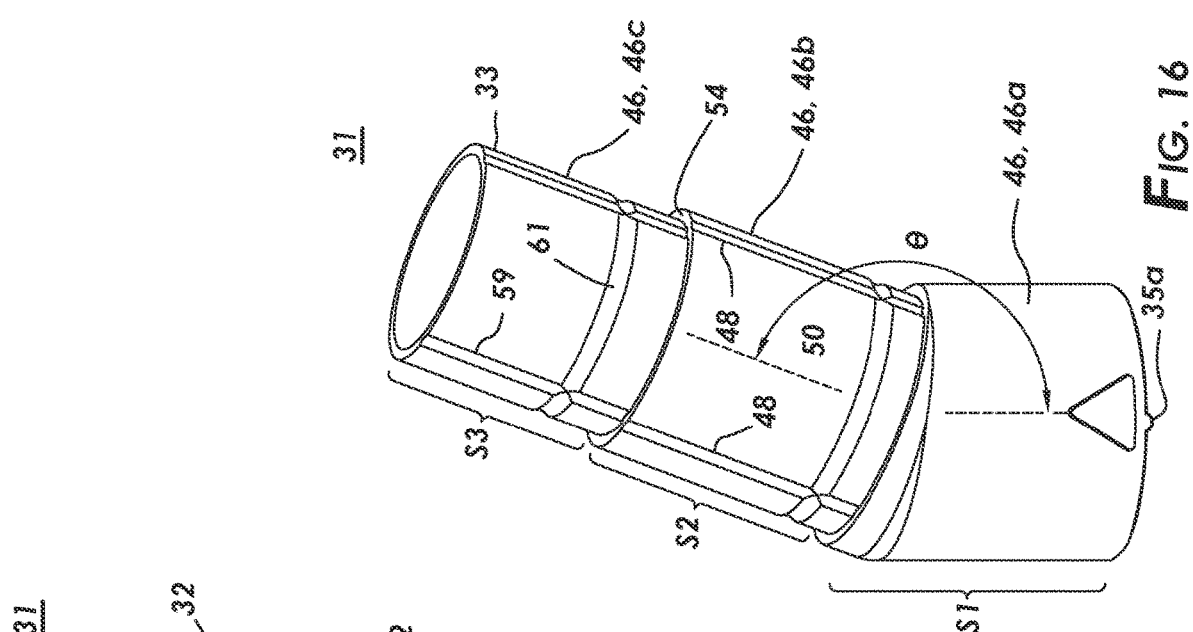
FIG. 16 is side elevation view of the hollow connector a having an external surface carrying mateable portions of a first keyed joint configured to arrest rotation of a face mask in relation to the hollow connector and a second keyed joint to configured to arrest rotation of hollow throat tube in relation to said hollow connector.

Now, with primary reference to FIGS. 1 through 16, particular embodiments of the airway assist device (1) can include a hollow connector (31) having a connector first end (32) opposite a connector second end (33). The connector first end (32) can carry a female thread (34) configured to threadably engage the male thread (13) of the barrel extension (7). There can be a substantial advantage in providing a removable hollow connector (31) to facilitate cleaning of the airway assist device (1) as compared to conventional devices in which the hollow connector (31) cannot be disassembled and cleaned. In particular embodiments, the barrel extension (7) and the connector first end (32) can further include mateable portions of a detent (35a, 35b) adapted to matingly engage upon correct treaded engagement of the hollow connector (31) to the barrel extension (7). Mated engagement of the portions of the detent (35a, 35b) arrests further rotation of the hollow connector (31) about the barrel extension (7). Forcible urging upon the hollow connector (31) in the opposite direction of rotation can overcome arrest of the portions of the detent (35a, 35b)

to allow the hollow connector (31) to be removed from the barrel extension (7). There can be a substantial advantage in providing the detent (35) to arrest rotation of the hollow connector (31) in relation to the barrel extension (7). In particular embodiments the hollow connector (31) can comprise an angled connector to dispose the connector second end (33) at an angle (θ) to the first connector end (32). As shown by the example of FIG. 16, the angle can have a degree measure of about 100° to about 170°. The degree measure can fall between the two ends of the range depending on the specific application. In the illustrative example of FIG. 16, the degree measure of the angle occurs in a range of about 150° to about 160°. In particular embodiments, the rotation arrest of the hollow connector (31) by the detent (35) disposes the connector second end (33) at an orientation to the barrel (2) for proper operation of the assembled airway assist device (1). Accordingly, where embodiments are to be disassembled and reassembled, the detent (35) assures that the hollow connector (31) can be assembled in correct fixed spatial orientation to the barrel extension (7) for proper operation of the airway assist device (1).

Now, with primary reference to FIGS. 1 through 20, in particular embodiments, a face mask (36) can be fluidically coupled to the first fluid pathway (9) defined by the barrel extension (7) outwardly extending from barrel distal end (4) directly or indirectly through the hollow connector (31). In the illustrative example of FIGS. 17 through 20, the face mask (36) can include a dome (37) extending to a dome outer periphery (38) which can be configured to engage a subject (S). A hollow stem (39) can outwardly extend from the dome (37) of the face mask (36). The hollow stem (39) can be configured to couple in fixed spatial relation or removably couple, directly or indirectly through the hollow connector (31) to barrel extension (7) outwardly extending from the barrel distal end (4) of the barrel (2). In particular embodiments, the dome (37) can comprise a sufficiently transparent or clear material allowing observation through the dome (37) of the subject (S) or the fluid or material (O) drawn up from a throat (T) of the subject (S). In particular embodiments, the dome outer periphery (38) can, but need not necessarily, engage an annular cuff (40). In particular embodiments, the annular cuff (40) can comprise a solid material having a density, hardness, or compression, or combination thereof, to conform to the subject's face (F) about the mouth (M) and nose (N). In particular embodiments, the annular cuff (39) can comprise an inflatable tubular member.

Now, with primary reference to FIGS. 11 and 17 through 19, in particular embodiments the annular cuff (40) can comprise a cuff annular body (41) arcuately extending between a annular body first edge (42) to an annular body second edge (43). The annular first edge (42) can be circumferentially coupled to the dome annular periphery (38) to dispose the second annular edge (43) radially inward of said dome annular periphery (38). The annular cuff (40) coupled to the dome annular periphery (38) presents a mask sealing cushion (44) configured to seal about the mouth (M) and nose (N) of a subject (S).

In embodiments, in which the face mask (36) and the hollow connector (31) comprise one piece, the connector first end (32) threadingly engaged to the barrel extension (7), with the mateable portions of the detent (35a, 35b) engaged, to dispose the face mask (36) in correct fixed spatial orientation to the barrel (2) of the airway assist device (1).

In embodiments, in which the face mask removably couples to the hollow connector second end (33), there can be a disadvantage of incorrectly orienting the face mask (36) in the correct fixed spatial orientation to the barrel (2) of the airway assist device (1). Incorrect spatial orientation of the face mask (36) in relation to the barrel (2) can result in inoperability of the airway assist device (1). As one illustrative example, if the face mask (36) is connected to a hollow connector (31) upside down and the hollow connector (31) has and angle (θ) between the connector first end (32) and the connector second end (33), then the handle (26) of the plunger (14) may be oriented in a direction that cannot be self-operated by the subject (S) chocking, or improperly operated, or operated ineffective to dislodge the object (O) in the throat (T) of the subject (S)

There would be a substantial advantage in having a hollow connector (31) and a face mask (36) removable from the hollow connector (31) that each carry mateable portions of a first keyed joint (45) that necessitates that the face mask (36) to the hollow connector (31) in the correct fixed spatial relationship for operation of the airway assist device (1).

Now, with primary reference to FIGS. 14 through 20, particular embodiments of the hollow connector (31) can have a hollow connector external surface (46) carrying a mateable portion of the first keyed joint (45) and the hollow stem (39) of the face mask (36) can have a hollow stem internal surface (47) carrying a mateable portion of the first keyed joint (45). In the illustrative example of FIGS. 14-16, the first keyed joint (45) can comprise one or more axial keyways (48) axially extending on the hollow connector external surface (46) and one or more axial keys (49) axially extending on the hollow stem internal surface (47). The one or more axial keys (49) can axially slidably engage the one or more axial keyways (48) to axially position the face mask (36) on the hollow connector (31) and arrest rotation of the face mask (36) in correct spatial relation to said hollow connector (31). Understandably, in particular embodiments, the hollow connector external surface (46) can carry one or more axial keys (49) and the hollow stem internal surface (47) can carry the one or more axial keyways (48).

Again, with primary reference to FIGS. 14 through 20, in particular embodiments, the hollow connector external surface (46) can further in include a circumferential keyway (50) configured to receive a circumferential key (51) disposed on the hollow stem internal surface (47). The circumferential keyway (50) and circumferential key (51) can mateably engage to arrest axial movement of the hollow stem (39) in relation to the hollow connector external surface (47). The circumferential key (51) can be disengaged from the circumferential keyway (50) by outward forcible urging of the face mask (36) to allow removal of the face mask (36) from the hollow connector (31). The face mask (36) can be reengaged to the hollow connector (31) by sliding axially engagement of the one or more axial keys (49) in the corresponding one or more axial keyways (50) to axially position the face mask (36) on the hollow connector (31) and arrest rotation of the face mask (36) in correct spatial relation to said hollow connector (31), and further forcible urging to mateably engage a circumferential key (51) with the circumferential keyway (50) to arrest axial movement of the hollow stem (39) in relation to the hollow connector external surface (46). Understandably, in particular embodiments the circumferential key (50) can be carried by the hollow connector external surface (46) and the circumferential keyway (50) can be carried by the hollow stem internal surface (47) of the face mask (36). In particular embodiments, the circumferential keyway (50) and the circumferential key (51) can comprise a continuous annular circumferential keyway mateable to a continuous annular circumferential key, as show in the illustrative examples of FIGS. 14 through 16 and 17-20; however, this illustrative example is not intended to preclude embodiments in which one or both of the circumferential keyway (50) and the circumferential key (51) include mateable discontinuous circumferential portions of the keyway (50) and discontinuous circumferential portions of the key (51). As an example, the circumferential key (51) can comprise an outward extending pin and the circumferential keyway (50) can comprise a pin socket.

Figure 15:
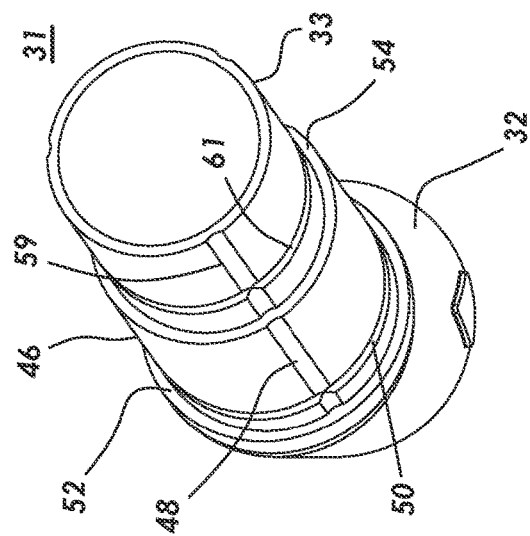
FIG. 15 is perspective view of a hollow connector second end having an external surface carrying mateable portions of a first keyed joint configured to arrest rotation of a face mask in relation to the hollow connector and a second keyed joint to configured to arrest rotation of hollow throat tube in relation to said hollow connector.
Figure 14:
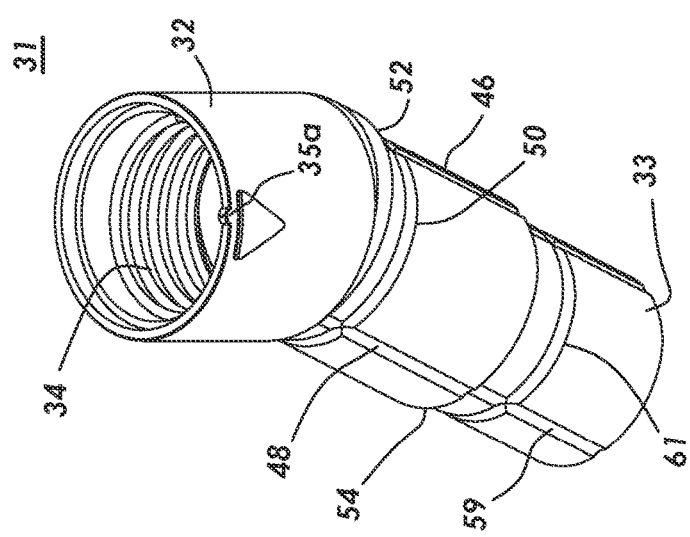
FIG. 14 is perspective view of a hollow connector having connector first end carrying a female thread configured to threadably engage a barrel extension carrying a male thread and having a hollow connector detent first portion adapted to matingly engage a barrel extension detent second portion to arrest rotation of said hollow connector threadably engaged to said barrel extension.
Figure 20:
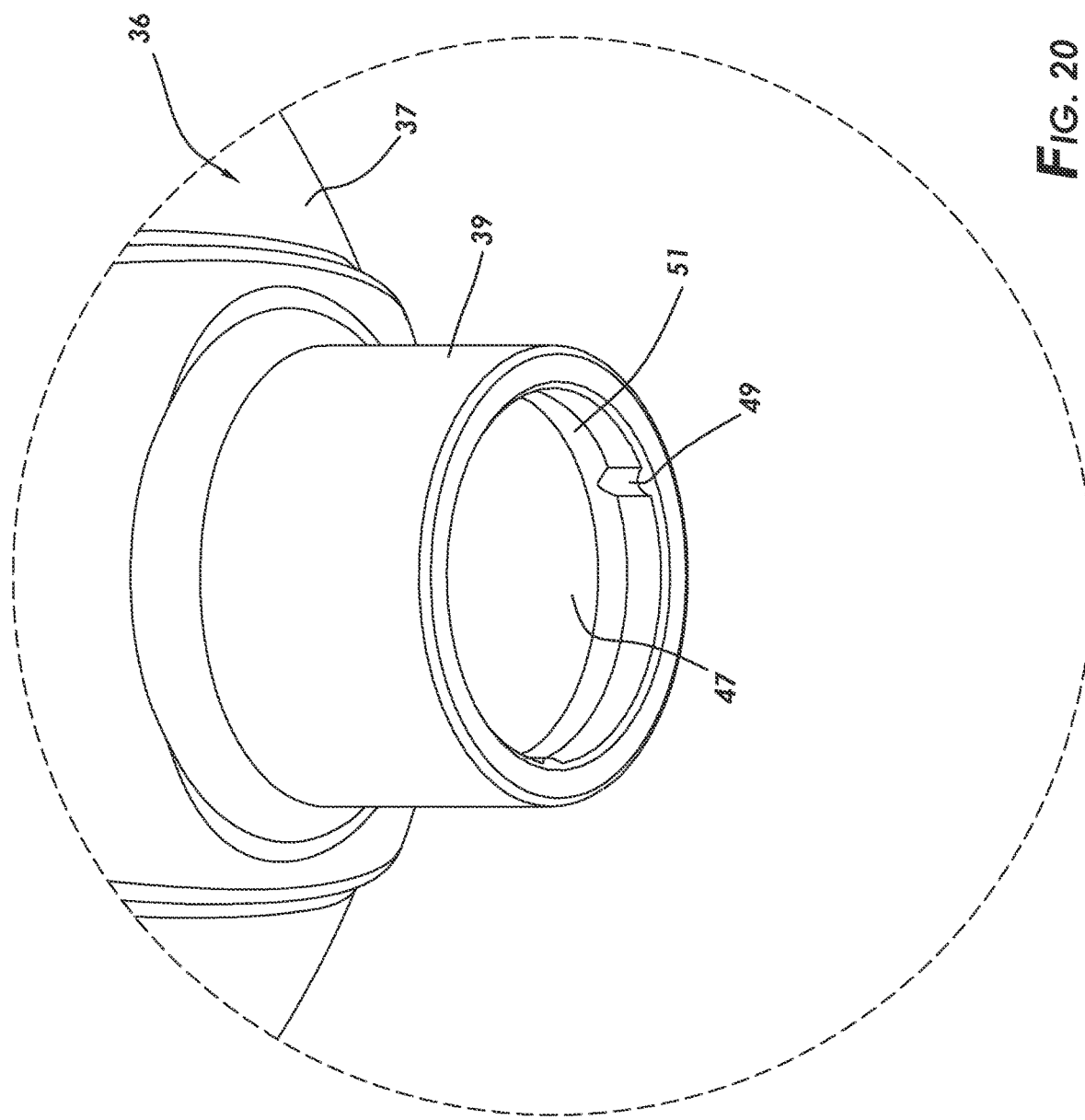
FIG. 20 is an enlarged view of FIG. 19 depicting the hollow stem of a particular embodiment of the face mask carrying mateable portions of the first key joint configured to arrest rotation of a face mask in relation to the hollow connector and second keyed joint configured to arrest axial travel of the face mask in relation to the hollow connector.

Now, with primary reference to FIGS. 14 through 16, in particular embodiments, a first segment of the hollow connector proximate the hollow connector first end (32) (as shown in the example of FIG. 16 as segment "S1") can have an first segment external surface (46a) having a greater dimension than a medial second segment of the hollow connector ("S2") having second segment external surface (46b) that carries the mateable portions of the first keyed joint (45) that engages the mateable portions of the first keyed joint (45) carried by the hollow stem internal surface (47). The transition between the first segment of the hollow connector (S1) and the second segment of the hollow connector (S2) defines an inwardly extending first annular shoulder (52) of the hollow connector (31). The hollow stem internal surface (47) having the mateable portions of the first keyed joint (45) can be engaged to the mateable portions of the first keyed joint (45) carried by the second segment of the hollow connector (S2) can further engage the first annular shoulder (52) to further assure arrest of axial movement of the face mask (36) in relation to the hollow connector (31).

In particular embodiments, the face mask (36) can, but need not necessarily, include a plurality of face masks (36) each having a hollow stem (29) carrying the mateable portions of the first keyed joint (45) to engage the mateable portions of the first keyed joint (45) carried by the hollow connector external surface (46b). Engagement of the mateable portions of the first keyed joint (45) assures that each of the plurality of face masks (36) can be disposed in the correct fixed spatial relation to the hollow connector (31) for operation of the airway assist device (1). The plurality of face masks (36) can be of the same size or can have a range of different sizes to correspondingly engage a plurality of subjects (S) of different anatomical size. Accordingly, a plurality of face masks (36) can be interchangeably coupled to the same airway assist device (1) for the purposes of replacement of lost or damaged face masks, maintain sterile conditions, or to fit the features or size of each of a plurality of subjects (S).

Now, with primary reference to FIGS. 1 through 11 and 16 through 22, particular embodiments the airway assist device (1) can further include a throat tube (53). The hollow connector (31) can further include a hollow connector third segment ("S3") disposed proximate the hollow connector second end (33) (as shown in the example of FIG. 16). The medial hollow connector second segment (S2) having second segment external surface (46b) can have a larger dimension than the hollow connector third segment (S3) having third segment external surface (46c). The transition between the hollow connector second segment (S2) and the hollow connector third segment (S3) defines an inwardly extending second annular shoulder (54) of the hollow connector (31). The hollow connector third segment external surface (46c) can be configured to mate with a throat tube (53) having a length disposed between a throat tube first end (55) and a throat tube second end (56). The throat tube (53) coupled to hollow connector third segment (S3) fluidically couples barrel interior chamber (6) the throat tube second end (56).

In the illustrative example of FIG. 11, the hollow stem (39) extending outward of the dome (37) of the face mask (36) slidably engages the hollow connector second segment (S2), and the hollow connector third segment (S3) slidably receives the throat tube first end (55). The assembly of the first hollow connector (31), the face mask (36), and the throat tube (53) can fluidically connect to the barrel interior chamber (6) to the throat tube second end (56).

Figure 21:
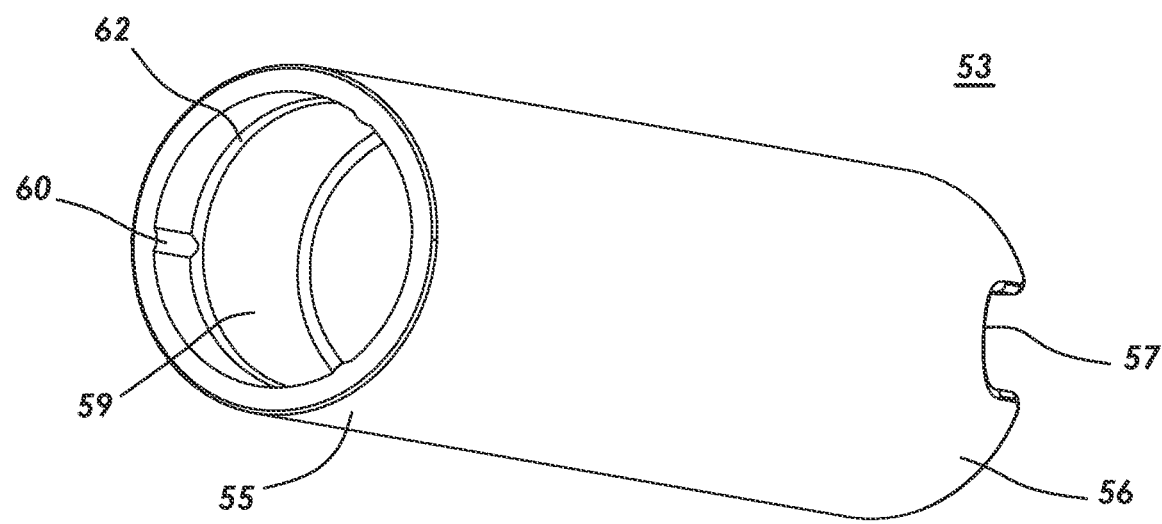
FIG. 21 is a perspective view of a first end of a particular embodiment of a hollow throat tube carrying mateable portions of the second key joint configured to arrest rotation and axial travel of the hollow throat tube in relation to the hollow connector.
Figure 22:
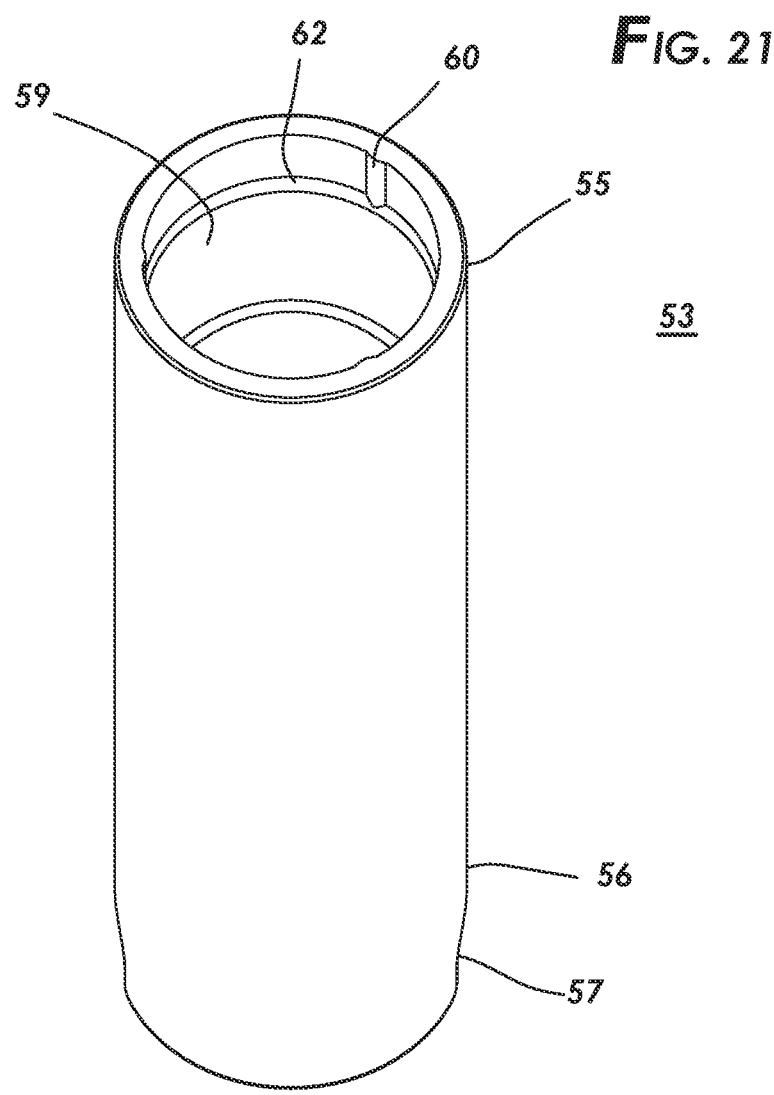
FIG. 22 is a perspective view of a first end of a particular embodiment of a hollow throat tube carrying mateable portions of the second key joint configured to arrest rotation and axial travel of the hollow throat tube in relation to the hollow connector.

Now, with primary reference to FIGS. 21 and 22, in particular embodiments, the throat tube (53) can, but need not necessarily, include one or more notches (57) open to the throat tube second end (56). The one or more notches (57) can assist in preventing the tongue (T) of the subject (S) from be drawn by suction into the throat tube second end (56) during outward movement of the plunger (14) in the barrel (2). In these particular embodiments, the one or more notches (57) can be oriented in a particular fixed spatial relation to the hollow connector (31) (as shown in the example of FIGS. 4 and 5). The hollow connector (31) can further include mateable portions of a second keyed joint (58) on the hollow connector third segment external surface (46c) and the throat tube first end internal surface (59) can carry mateable portions of the second keyed joint (58).

In the illustrative example of FIGS. 14 through 16 and 21 through 22, the second keyed joint (58) can comprise one or more axial keyways (59) disposed in the hollow connector third segment external surface (46c) and one or more axial keys (60) axially disposed on the throat tube first end internal surface (59). The one or more axial keys (60) can axially slidably engage the one or more axial keyways (59) to axially position the throat tube (53) on the hollow connector third segment external surface (46c) and arrest rotation of the throat tube (53) in correct spatial relation to said hollow connector (31). Understandably, in particular embodiments, the hollow connector third segment external surface (46c) can carry one or more axial keys (60) and the throat tube first end internal surface (59) of the throat tube (53) can carry the one or more axial keyways (59).

In particular embodiments, the hollow connector third segment external surface (46c) can further in include a circumferential keyway (61) configured to receive a circumferential key (62) disposed on the throat tube first end internal surface (59). The circumferential keyway (61) and circumferential key (62) can mateably engage to arrest axial movement of the throat tube (53) in relation to the hollow connector third segment external surface (46c). The circumferential key (62) can be disengaged from the circumferential keyway (61) by outward forcible urging of the throat tube (53). The throat tube (53) can be reengaged to the hollow connector third segment (S3) by sliding axially engagement of the one or more axial key (62) along the corresponding one or more axial keyways (59) to axially position the throat tube (53) on the hollow connector (31) and arrest rotation of the throat tube (43) in correct spatial relation to the hollow connector (31), and by further forcible urging to mateably engage circumferential key (62) with the circumferential keyway (61) to arrest axial movement of the throat tube (53) in relation to the hollow connector third segment external surface (46c). Understandably, in particular embodiments the circumferential key (62) can be carried by the hollow connector third segment external surface (46c) and the circumferential keyway (61) can be carried by the throat tube first end internal surface (59). In particular embodiments, the circumferential keyway (61) and the circumferential key (62) can comprise a continuous annular circumferential keyway mateable to a continuous annular circumferential key, as shown in the illustrative examples of FIGS. 14-16 and 21 and 22; however, this illustrative example is not intended to preclude embodiments in which one or both of the circumferential keyway (61) and the circumferential key (62) include mateable discontinuous circumferential portions of keyway (61) and discontinuous circumferential portions of the key (62). As an example, the circumferential key (62) can comprise an outward extending pin and the circumferential keyway can comprise a pin socket. In particular embodiments, the throat tube (53) can, but need not necessarily, curve approaching the tube second end (56) to assist in advancement of the throat tube (53) into the curvature of the airway (A).

Figure 23:
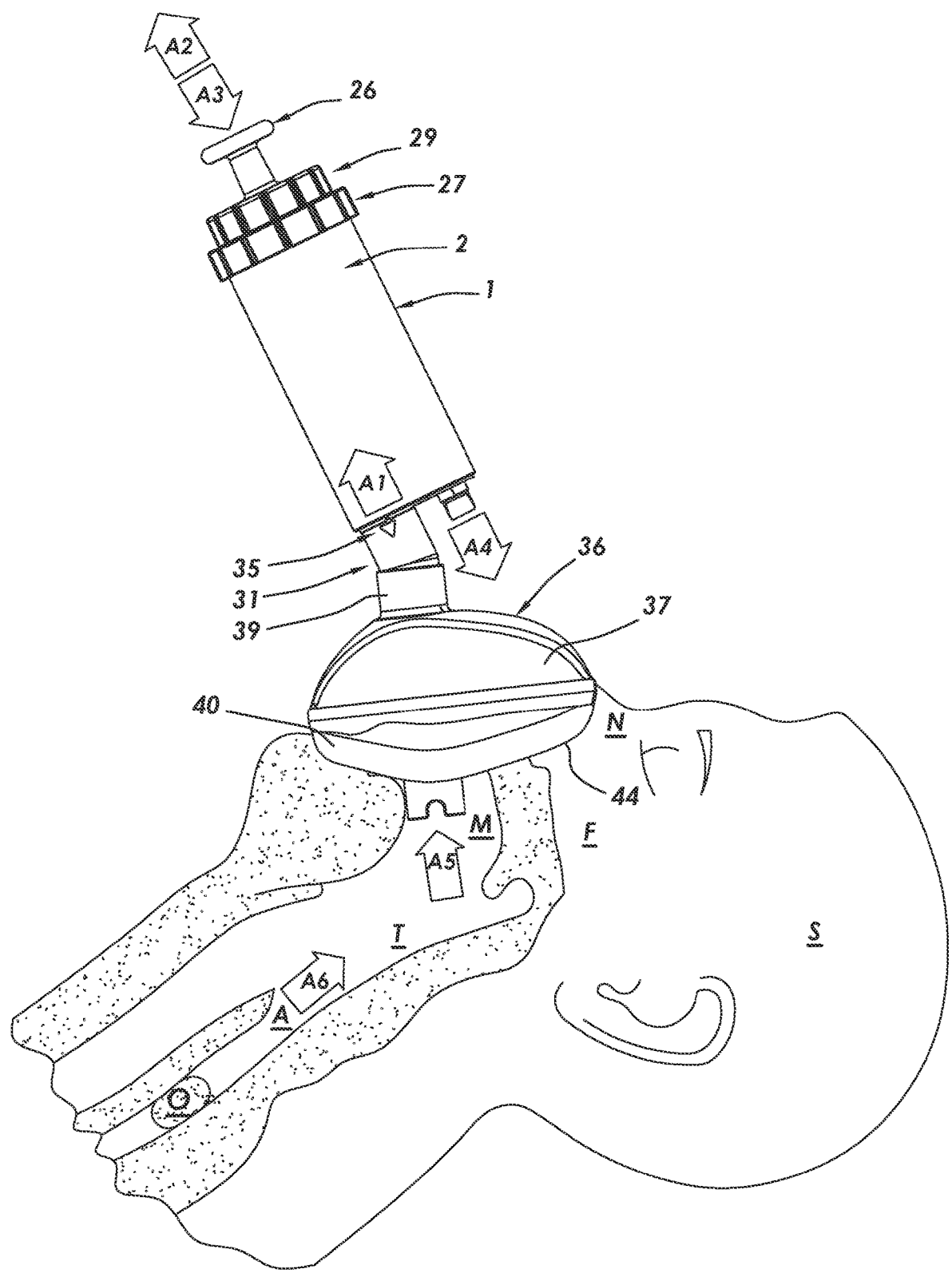
FIG. 23 is an illustration of a method of using embodiments of the airway assist device to dislodge objects from the throat of a subject.

Now, with primary reference to FIGS. 10 through 12 and 23, in particular embodiments a first one-way valve (63) can, but need not necessarily, be disposed to regulate airflow (depicted as arrow A1) through the barrel extension (7) at barrel distal end (4) when the plunger moves outward within the barrel (depicted by arrow A2). The first one-way valve (63) can reduce or prevent airflow from passing outward of the barrel extension (7) from the barrel interior chamber (6) when the plunger (14) moves inward (depicted as arrow A3) within the barrel (2) toward the barrel distal end (4) (as shown in the example of FIG. 23). In particular embodiments, the first one-way valve (63) can, but need not necessarily be, duck bill valves as depicted in the Figures and the first one-way valve (63) can be in the form of any type of one way valve, such as: check valves, clack valves, non-return valves, reflux valves, retention valves, diaphragm valves, ball check valves, swing check valve, flapper valves or the like.

Now, with primary reference to FIG. 12, in particular embodiments the barrel distal end (4) can be configured to allow the first-one way valve (63) to be overmolded the barrel distal end (4) inside of the barrel extension (7) and extending into the barrel chamber (6). In these particular embodiments, the overmold process affixes a first one-way valve base (64) to the barrel extension internal surface (8) to dispose the valve cuspids (65) inward of the barrel interior chamber (6). In particular embodiments, the barrel distal end (4) can be configured to dispose a concentric annular member (66) proximate the barrel extension internal surface (8) to afford a concentric annular passage (67) between the barrel extension internal surface (8) and the concentric annular member (66). The concentric annular passage (67) allows molten thermoplastic elastomer to flow through the concentric annular passage (67) into the barrel chamber (6) to allow a first one-way valve retainer (68) to be formed inside the barrel interior chamber (6) and extending over the concentric annular passage (67) between the barrel extension internal surface (8) and the concentric annular member (66). In particular embodiments, the overmolded first-one way valve (63) can be formed as a split duckbill valve (63a) as shown in the illustrative example of FIG. 12.

Again, with primary reference to FIG. 12, the barrel distal end (4) can further include a second opening (69) defining a second fluid pathway (70) into the barrel interior chamber (6). A second one-way valve (71) can, but need not necessarily, be disposed to regulate airflow (depicted by arrow A4) through the second opening (69) in the barrel distal end (4) of the barrel (2) (as shown in the example of FIG. 23). The second one-way valve (71) can reduce or prevent airflow from passing inward of the second opening (69) into the barrel interior chamber (6) when the plunger (14) moves outward (depicted by arrow A2) within the barrel (2) toward the barrel proximal end (3). In particular embodiments, the second one-way valve (72) can, but need not necessarily be, duck bill valves as depicted in the illustrative example of FIG. 12; however, the second one-way valve (71) can be in the form of any type of one way valve, such as: check valves, clack valves, non-return valves, reflux valves, retention valves, diaphragm valves, ball check valves, swing check valve, flapper valves, or the like.

Again, with primary reference to FIG. 12, in particular embodiments, the barrel distal end (4) can be configured to allow the second one-way valve (71) to be overmolded to the barrel distal end (4) over the second opening (69) and extending outward of the barrel distal end (4). In these particular embodiments, the overmold process affixes a second one-way valve base (73) to the barrel distal end (4) to dispose the second one-way valve cuspids (74) outward of the barrel distal end (4). In particular embodiments, the barrel distal end (4) can be configured to dispose a concentric annular member (75) within the second opening (69) to afford a concentric annular passage (76) between the barrel opening (69) and the concentric annular member (76). The concentric annular passage (76) allows molten thermoplastic elastomer flow through the concentric annular passage (76) into the barrel chamber (6) to allow a second one-way valve retainer (77) to be formed inside the barrel interior chamber (6) and extending over the concentric annular passage (76) and a portion of the barrel internal surface (5). In particular embodiments, the overmolded second-one way valve (71) can be a duckbill valve as shown in the illustrative example of FIG. 12.

Figure 8:
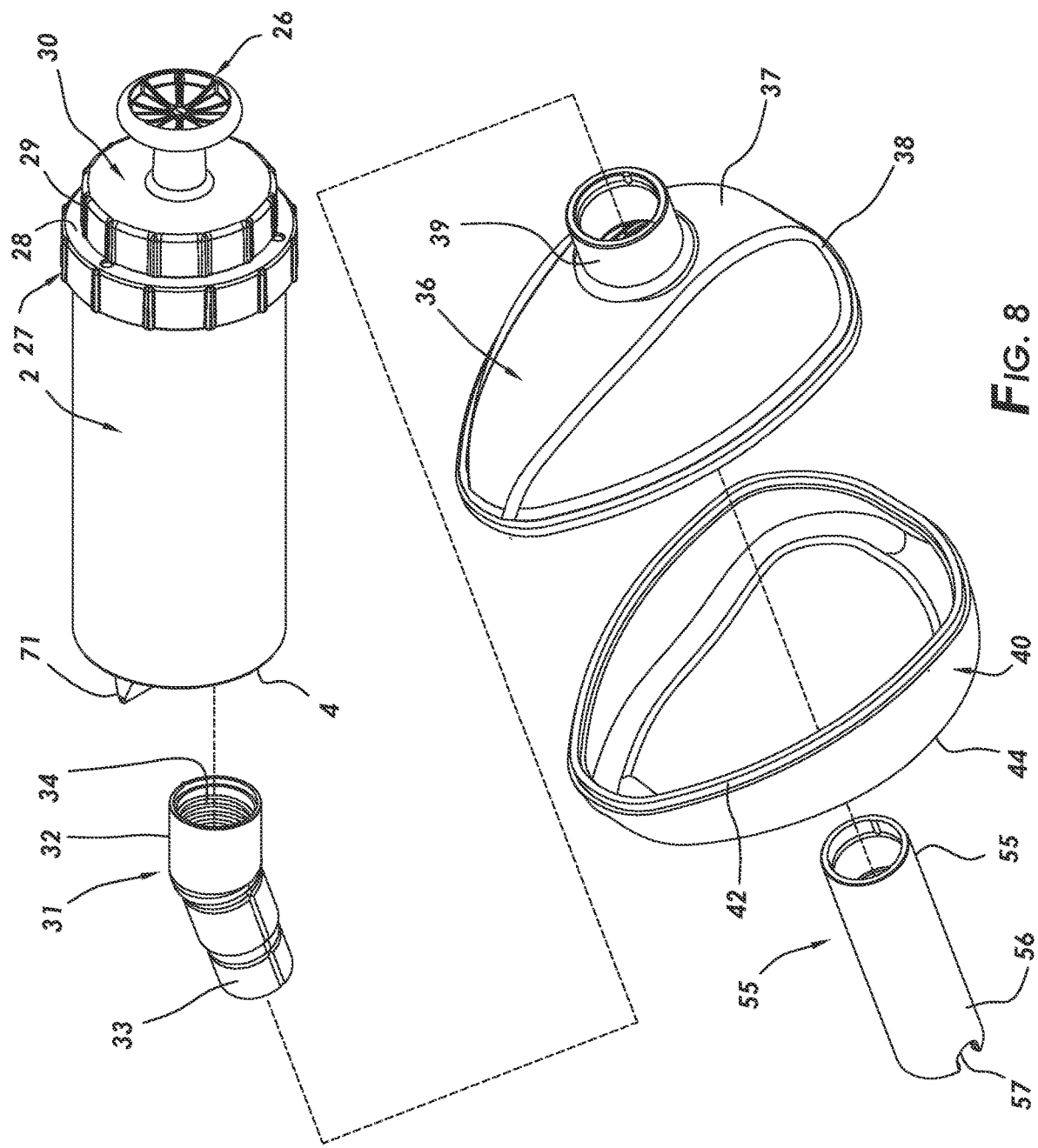
FIG. 8 is an exploded perspective view depicting the keyed interlocking components of the particular embodiment of the airway assist device as shown in FIG. 1.
Figure 9:
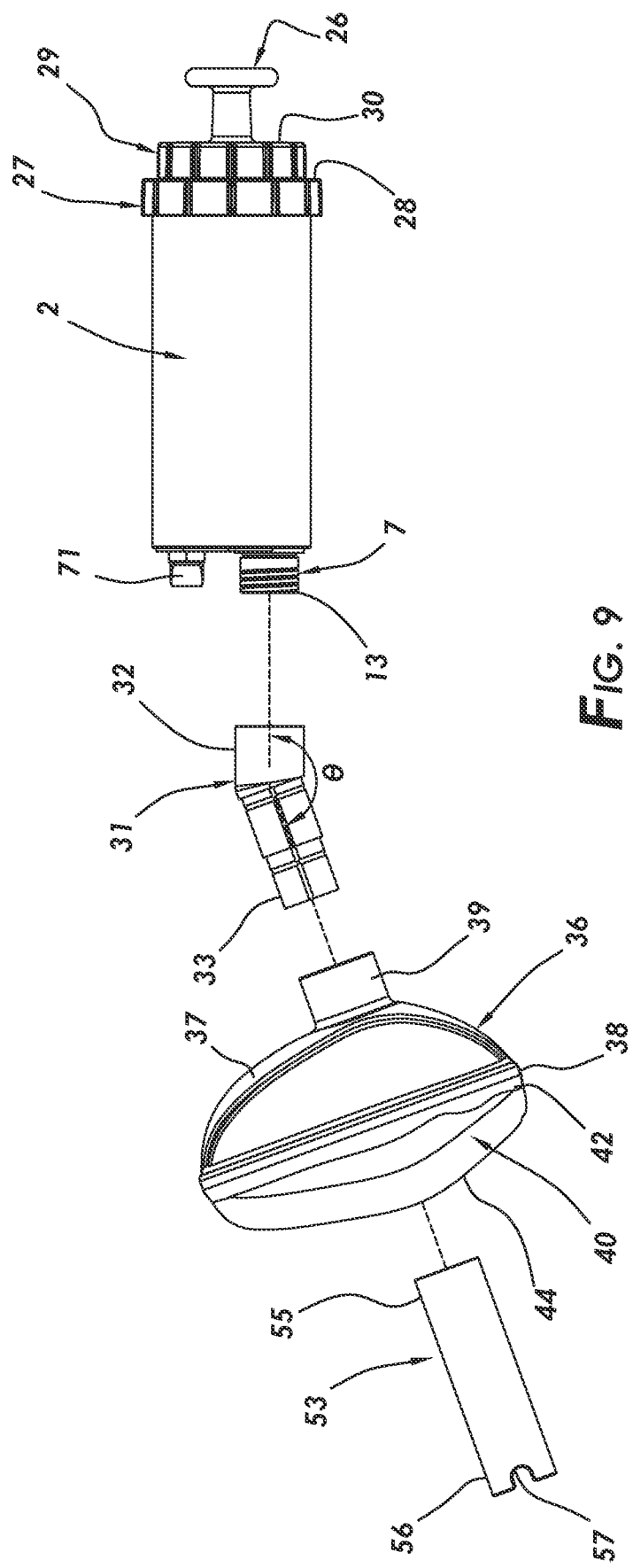
FIG. 9 is an exploded side elevation view depicting the keyed interlocking components of the particular embodiment of the airway assist device as shown in FIG. 1.

Now with primary reference to FIGS. 8 and 9, a method of using embodiments of the airway assist device (1) can comprise, consist essentially of, or consist of one or more of: slidably engaging the plunger (14) in the barrel (2) (as depicted by arrows A2 and A3). Pushing the plunger (14) inwardly in the barrel (2) toward the barrel distal end (4) until the plunger distal end (16) has a location proximate the barrel distal end (4) of the barrel (2) (as depicted by arrow A3). Coupling a hollow connector (31) to the barrel extension (7) outwardly extending from a barrel distal end (4), and in particular embodiments, threadingly engaging the hollow connector first end (32) carrying a female thread (34) with the barrel extension (7) carrying a male thread (13), and in particular embodiments, rotating the hollow connector (31) until the mated portions of a detent (35a, 35b) engage to dispose the hollow connector (31) in fixed spatial relation to the barrel (2). Coupling a face mask (36) to the hollow connector second end (33), and in particular embodiments, slidably engaging mateable portions of a first keyed joint (35) carried by the face mask hollow stem (39) to mateable portions of the first keyed joint (35) carried by the medial second segment (S2) of the hollow connector (31) to arrest rotation of the face mask (36) about the hollow connector (31), and in particular embodiments, forcibly urging the face mask (36) axially along the medial second segment (S2) of the hollow connector (31) to engage mateable portions of the first keyed joint (35) carried by the hollow stem (39) of the face mask (36) to mateable portions of the first keyed joint (35) carried by the medial second segment (S2) of the hollow connector (31) to arrest axial movement of the face mask (36) along the hollow connector (31). Coupling the throat tube (53) to the hollow connector second end (33), and in particular embodiments, slidably engaging mateable portions of a second keyed joint (58) carried by the throat tube (53) to mateable portions of the second keyed joint (58) carried by a third segment (S3) of the hollow connector (31) to arrest rotation of the throat tube (53) about the hollow connector (31), and in particular embodiments, forcibly urging the throat tube (53) axially along the third segment (S3) of the hollow connector (31) to engage mateable portions of the second keyed joint (58) carried by the throat tube (53) to mateable portions of the second keyed joint (58) carried by the medial second segment (S2) of the hollow connector (31) to arrest axial movement of the face mask (36) along hollow connector (31). Disassembling the airway assist device (1) in reverse order to the assembly of the airway assist device (1).

Again, with primary reference to FIG. 23, the method of using embodiments of the airway assist device (1) can comprise, consist essentially of, or consist of one or more of: inserting the throat tube (53) into the throat (T) of the subject (S). The method can further comprise engaging the face mask (36) about the mouth (M) and nose (N) of the subject (S), wherein the throat tube (53) can be dimensioned such that once the face mask (36) engages the face (F) of the subject (S), the throat tube second end (56) has the proper location in the throat (T) of the subject (S). Accordingly, the configuration of the mask (36) in relation to the configuration of the throat tube (T) acts as a stop and prevents over insertion of the throat tube (39) into the throat (T) which can cause the fluid or other material (O) to be pushed deeper into the subject's airway (A). Upon proper positioning of the throat tube (53) within the person's throat (T), drawing the plunger (14) slidably disposed within the barrel (2) (depicted by arrow A2) to generate a suction in the throat tube (53) which causes air to be drawn into the throat tube second end (56) (depicted by arrow A5). The air drawn into the throat tube second end (56) assists in dislodging, expelling or drawing the fluid or other material (O) up and out of the throat (T) (as depicted by arrow A6). In particular embodiments, a retainer ring (27) can prevent the plunger (14) from being removed from within the barrel (2). The transparency of the material of the dome (37) of the face mask (36) can allow the subject (S) or fluids and materials (O) to be observed through the dome (37). As one example, if the subject (S) has vomited or if fluid or material (O) has been transferred to the barrel interior chamber (6) of the barrel (2), the method can then further comprise removing the throat tube (53) from the throat (T) of the subject (S), and inwardly pushing the plunger (14) in said barrel (2) to generate a positive pressure in the barrel (2) (depicted by arrow A6) and expelling the fluid or material (O) from said barrel (2) through the second opening (69) in the barrel distal end (4) or through the second one-way valve (74) (depicted by arrow A11). The method can be repeated with or without removal of throat tube from the throat (T).

As can be easily understood from the foregoing, the basic concepts of the present invention may be embodied in a variety of ways. The invention involves numerous and varied embodiments of an airway assist device (1) and methods for making and using such airway assist device (1) including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "connector" should be understood to encompass disclosure of the act of "connecting"—whether explicitly discussed or not—and, conversely, were there is a disclosure of the act of "connecting", such a disclosure should be understood to encompass disclosure of a "connector" and even a "means for connecting". Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Further, for the purposes of the present invention, the term "coupled" or derivatives thereof can mean indirectly coupled, coupled, directly coupled, connected, directly connected, or integrated with, depending upon the embodiment.

Additionally, for the purposes of the present invention, the term "integrated" when referring to two or more components means that the components (i) can be united to provide a one-piece construct, a monolithic construct, or a unified whole, or (ii) can be formed as a one-piece construct, a monolithic construct, or a unified whole. Said another way, the components can be integrally formed, meaning connected together so as to make up a single complete piece or unit, or so as to work together as a single complete piece or unit, and so as to be incapable of being easily dismantled without destroying the integrity of the piece or unit.

Thus, the applicant(s) should be understood to claim at least: i) each of the airway assist device herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon. The elements following an open transitional phrase such as "comprising" may in the alternative be claimed with a closed transitional phrase such as "consisting essentially of" or "consisting of" whether or not explicitly indicated the description portion of the specification.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. An airway assist device, comprising:
   a barrel having a barrel proximal end and a barrel distal end, said barrel distal end having a barrel extension outwardly extending from said barrel distal end, said barrel extension having an internal surface defining a fluid pathway open to a barrel interior chamber, and an external surface carrying a male thread;
   a plunger slidably disposed within said barrel;
   a hollow connector having a connector first end opposite a connector second end, said connector first end carrying a female thread configured to threadably engage said male thread of said barrel extension,
      wherein said barrel extension and said connector first end include portions of a detent adapted to matingly engage to arrest rotation of said hollow connector threadably engaged to said barrel extension,
      wherein said hollow connector comprises an angled connector, wherein upon engagement of said portions of said detent said hollow connector and said barrel are disposed in a fixed angled spatial relation; and
   a face mask having a hollow stem configured to couple to said hollow connector, said face mask adapted to seal about a mouth and a nose of a subject, wherein upon engagement of said portions of said detent said hollow connector and said barrel are disposed in fixed spatial relation.

2. The device of claim 1, wherein said hollow connector having a hollow connector external surface and said hollow stem having a hollow stem internal surface each carrying mateable portions of a first keyed joint configured to arrest rotation of said face mask in relation to said hollow connector.

3. The device of claim 2, wherein said first keyed joint comprises a first axial keyway disposed in said hollow connector external surface of said hollow connector and a first axial key disposed on said hollow stem internal surface of said hollow stem, said first axial key slidably engages said first axial keyway to couple said face mask to said hollow connector.

4. The device of claim 2, wherein said first keyed joint comprises a first circumferential keyway disposed in said hollow connector external surface of said hollow connector and a first circumferential key disposed on said hollow stem internal surface of said hollow stem, said first circumferential key urged axially along said hollow connector external surface to mateably engage said first axial keyway to couple said face mask to said hollow connector.

5. The device of claim 2, wherein upon engagement of said mateable portions of first keyed joint, said face mask is disposed in fixed spatial relation to said hollow connector.

6. The device of claim 2, wherein upon engagement of said mateable portions of said detent and wherein upon engagement of said mateable portions of said first keyed joint, said face mask, said hollow connector and said barrel disposed in fixed spatial relation.

7. The device of claim 2, wherein mateable portions of said first keyed joint having dimensions common among a plurality of face masks allowing interchange between said plurality of face masks and said hollow connector, wherein upon engagement of said mateable portions of said keyed joint carried by any one of said plurality of face masks and said hollow connector, each of said plurality of masks is disposed in substantially the same fixed spatial relation to said hollow connector.

8. The device of claim 2, wherein said hollow connector external surface has a first circumferential shoulder inwardly extending from a hollow connector first segment carrying said female thread connected to a second segment of lesser dimension carrying mateable portions of said first keyed joint.

9. The device of claim 8, wherein upon engagement of said mateable portions of said first keyed joint said hollow stem of said face mask seats against said first shoulder.

10. The device of claim 2, further comprising a hollow throat tube coupled to said hollow connector second end.

11. The device of claim 10, wherein said hollow connector having a hollow connector external surface and said throat tube having a throat tube internal surface each carrying mateable portions of a second keyed joint configured to arrest rotation of said throat tube in relation to said hollow connector.

12. The device of claim 11, wherein said second keyed joint comprises a second axial keyway disposed in said hollow connector external surface of said hollow connector and a second axial key disposed on a throat tube first end internal surface of said throat tube, said second axial key slidably engages said second axial keyway to couple said throat tube to said hollow connector.

13. The device of claim 12, wherein said second keyed joint further comprises a first circumferential keyway disposed in said hollow connector external surface of said hollow connector and a first circumferential key disposed on said throat tube first end internal surface of said throat tube, said second circumferential key urged axially along said hollow connector external surface to mateably engage said second circumferential keyway to couple said throat tube to said hollow connector.

14. The device of claim 13, wherein said hollow connector external surface has a second circumferential shoulder inward extending from said hollow connector second segment to a hollow connect third segment of lesser dimension carrying mateable portions of said second keyed joint.

15. The device of claim 14, wherein upon engagement of said mateable portions of said second keyed joint said throat tube first end of said throat tube seats against said second shoulder.

16. The device of claim 13, further comprising one or more notches disposed at said throat tube second end, wherein upon engagement of said second key joint said one or more notches held in fixed spatial relation to said hollow connector.

* * * * *